(12) United States Patent
Wang et al.

(10) Patent No.: US 7,964,355 B2
(45) Date of Patent: Jun. 21, 2011

(54) ASSAYS BASED ON DETECTION OF PHOTOBLEACHING REACTION PRODUCTS FROM DYE CATALYTIC COMPLEX

(75) Inventors: Maiomiao Wang, Castro Valley, CA (US); Rachel Anne Holmes-Davis, La Cañada Flintridge, CA (US); Rick Blidner, Emeryville, CA (US); Zbigniew Rafinski, Golub-Dobrzyn (PL); Beata Anna Jedrzejewska, Bydgoszcz (PL); Jerzy Paczkowski, Bydgoszcz (PL); Brian David Warner, Martinez, CA (US); Heather Koshinsky, El Cerrito, CA (US)

(73) Assignee: Investigen, Inc., Hercules, CA (US)

( * ) Notice: Subject to any disclaimer, the term of this patent is extended or adjusted under 35 U.S.C. 154(b) by 0 days.

(21) Appl. No.: 12/372,439

(22) Filed: Feb. 17, 2009

(65) Prior Publication Data

US 2010/0209909 A1 Aug. 19, 2010

(51) Int. Cl.
*C12Q 1/68* (2006.01)
*C07H 21/02* (2006.01)
(52) U.S. Cl. .......................... 435/6; 536/23.1
(58) Field of Classification Search ..... 435/6; 536/22.1, 536/23.1
See application file for complete search history.

(56) References Cited

U.S. PATENT DOCUMENTS

| | | | |
|---|---|---|---|
| 5,034,506 | A | 7/1991 | Summerton et al. |
| 5,340,716 | A * | 8/1994 | Ullman et al. ............ 435/6 |
| 5,641,625 | A | 6/1997 | Ecker et al. |
| 5,705,333 | A | 1/1998 | Shah et al. |
| 5,714,331 | A | 2/1998 | Buchardt et al. |
| 5,719,262 | A | 2/1998 | Buchardt et al. |
| 5,736,336 | A | 4/1998 | Buchardt et al. |
| 5,766,855 | A | 6/1998 | Buchardt et al. |
| 5,773,571 | A | 6/1998 | Nielsen et al. |
| 5,786,461 | A | 7/1998 | Buchardt et al. |
| 6,107,470 | A | 8/2000 | Nielsen et al. |
| 6,225,052 | B1 * | 5/2001 | Batz et al. ............... 435/6 |
| 6,228,982 | B1 | 5/2001 | Norden et al. |
| 6,357,163 | B1 | 3/2002 | Buchardt et al. |
| 6,403,763 | B1 | 6/2002 | Loew |
| 6,414,112 | B1 | 7/2002 | Buchardt et al. |
| 6,441,130 | B1 | 8/2002 | Egholm et al. |
| 6,451,968 | B1 | 9/2002 | Egholm et al. |
| 2003/0157500 | A1 | 8/2003 | Lowe |
| 2003/0162699 | A1 | 8/2003 | Lowe |
| 2007/0231821 | A1 * | 10/2007 | Bupp et al. ............. 435/6 |

FOREIGN PATENT DOCUMENTS

WO WO 2005017181 A2 2/2005
WO WO 2007100711 A2 * 9/2007

OTHER PUBLICATIONS

Antony T., et al., "Molecular Beacons: Nucleic Acid Hybridization and Emerging Applications," *J Biom Struct. & Dyn.*, 19(3):497-504 (2001).

Armitage, B., "Cyanine-Dye-DNA Interactions: Intercalation, Groove Binding, and Aggregation," *Top Curr Chem*, 253:55-76 (2005).
Jimenez-Banzo, et al., "Time-Resolved Methods in Biophysics. 7. Photon Counting vs. Analog Time-Resolved Singlet Oxygen Phosphorescence Detection," *Photochem Photobiol Sci*, 7:1003-1010 (2008).
Baeumner, et al., "A Universal Nucleic Acid Sequence Biosensor with Nanomolar Detection Limits," *Anal. Chem.*, 76(4):888-894 (2004).
Barta, C., et al., "Dansyl-And Rhodamine-Based Fluorescent Sensors for Detecting Singlet Oxygen and Superoxide Production in Plants in Vivo," *Proceedings of the 7th Hungarian Congress on Plant Physiology*, 46(3-4):149-150 (2002).
Bentin, T, et al., "Superior Duplex DNA Strand Invasion by Acridine Conjugated Peptide Nucleic Acids," *J. Am Chem Soc*, 125(21):6378-6379 (2003).
Berger, M., "High performance liquid chromatography-electrochemical assay for monitoring the formation of 8-oxo-7,8-dihydroadenine and its related 2'-deoxynucleoside.," *J. Liquid Chromatogr.*, 13, 929-932 (1990).
Biver T., et al., "Cyanine Dyes as Intercalating Agents: Kinetic and Thermodynamic Studies on the DNA/Cyan40 and DNA/Ccyan2 Systems," *Biophy J*, 89:374-383 (2005).
Cell Biology: A Laboratory Handbook, J.E. Celis ed., vol. 2, Academic Press (1998).
Chandler, D., et al., "Affinity Capture and Recovery of DNA at Femotomolar Concentrations with Peptide Nucleic Acid Probes," *Analytical Biochemistry*, 283:241-249 (2000).
Chibisov, A.K., et al., "Photoprocesses in Dimers of Thiacarbocyanines," *Phys Chem Chem Phys*, 1:1455-1460 (1999).
Demidov, V., et al., "Kinetics and Mechanism of the DNA Double Helix Invasion by Pseudocomplementary Peptide Nucleic Acids," *Proc Natl Acad Sci*, 99(9):5953-5958 (2002).
Demidov, V.V.,et al., "Duplex DNA capture," *Current. Issues in Mol. Bio.* 2(1):31-35 (2000).
Demidov, V., et al., "Kinetics and Mechanism of Polyamide ("Peptide") Nucleic Acid Binding to Duplex DNA," *Proc. Natl. Acad. Sci. USA*, 92:2637-2641 (1995).
Dilek, I., et al., "Effect of PNA Backbone Modifications on Cyanine Dye Binding to PNA-DNA Duplexes Investigated by Optical Spectroscopy and Molecular Dynamics Simulations," *J Am Chem Soc*, 127: 3339-3345 (2005).
Dizdaroglu, M., "Chemical Determination of Free Radical-Induced Damage to DNA," *Free Rad Biol. Med.*, 10:225-242 (1991).

(Continued)

*Primary Examiner* — Suryaprabha Chunduru
(74) *Attorney, Agent, or Firm* — Brinks Hofer Gilson & Lione

(57) ABSTRACT

The present invention relates to the methods for assaying an analyte comprising a nucleic acid analog binding substrate in a sample, comprising reacting a catalytic complex comprising a nucleic acid analog, a nucleic acid analog specific binding substrate and a light reactive dye with a light stimulus, and detecting the presence or absence or amount of a reaction product of the catalytic complex and light stimulus. The present invention also relates to a method of assaying a nucleic acid analyte in a sample using an analyte-specific reporter complex. The present invention also relates to a method of assaying an analyte in a sample using a reporter molecule.

28 Claims, 10 Drawing Sheets

OTHER PUBLICATIONS

Egholm M., et al., "PNA Hybridizes to Complementary Oligonucleotides Obeying the Watson-Crick Hydrogen-Bonding Rules," *Nature*, 365:566-568 (1993).

Floyd, R.A., et al., "Hydroxyl Free Radical Adduct of Deoxyguanosine: Sensitive Detection and Mechanism of Formation," *Free Rad. Res. Commun.*, 1(3):163-172 (1986).

Freshney, R.I., Animal Cell Culture (1987).

Geiger, A., et al., "PNA Array Technology in Molecular Diagnostics," *Nucleosides & Nucleotides*, 17(9-11):1717-1724 (1998).

Glazer, A.N. et al., "Stable Dyne-DNA Intercalation Complexes as Reagents for High-Sensitivity Fluorescence Detection," *Nature*, 359:859-861 (1992).

Gomes A., et al., "Fluorescence probes Used for Detection of Reactive Oxygen Species," *J Biochem Biophys Methods*, 65:45-80 (2005).

Hannah K.C., et al., "$^1$H NMR and Optical Spectroscopic Investigation of the Sequence-Dependent Dimerization of a Symmetrical Cyanine Dye in the DNA Minor Groove," *Biochemistry*. 44:15924-15929 (2005).

Hoebeke M., et al., "Singlet Oxygen Production of Photoisomerization: Two Competitive Processes for Merocyanine 540 Irradiated with Visible Light," *J. Photochem. Photobio., B. Biology*, 1:437-446 (1988).

Jensen, K., et al., "Kinetics for Hybridization of Peptide Nucleic Acids (PNA) with DNA and RNA Studies with the BIAcore Technique," *Biochemistry*, 36:5072-5077 (1997).

Kaihatsu, K., et al., "Enhanced Strand Invasion by Peptide Nucleic Acid—Peptide Conjugates," *Biochemistry*, 41(37):11118-11125 (2002).

Khan, A.U., et al., "Director Spectroscopic Observation of Singlet Oxygen Emission at 1268 nm Excited by Sensitizing Dyes of Biological Interest in Liquid Solution," *Proc Natl Acad Sci USA*, 76(12):6047-6049 (1979).

Kielkopf, C. L., et al., "A Structural Basis for Recognition of A-T and T-A Base Pairs in the Minor Groove of B-DNA," *Science*, 282(5386):111-115 (1998).

Komiyama, et al., "PNA for One-Base Differentiating Protection of DNA from Nuclease and its Use for SNPs Detection," *J Am Chem Soc*, 125:3758-3762 (2003).

Kuhn H., et al., "Hybridization of DNA and PNA Molecular Beacons to Single-Stranded and Double-Stranded DNA Targets," *J Am Chem Soc*, 124(6):1097-1103 (2002).

Lartia, et al., "New Cyanine-Oligonucleotide Conjugates: Relationships between Chemical Structures and Properties," *Chem. Eur. J.*, 12:2270-2281 (2006).

Larsen H., et al., "Antisense Properties of Peptide Nucleic Acid," *Biochim et Biophys Acta*, 1489:159-166 (1999).

Lee L., et al., "Thiazole Orange: A New Dye for Reticulocyte Analysis," *Cytometry*, 7:508-517 (1986).

Lion, Y., et al., "New Method of Detecting Singlet Oxygen Production," *Nature*, 263:442-443 (1976).

Lohse, J., et al., "Double Duplex Invasion by Peptide Nucleic Acid: A General Principle for Sequence-Specific Targeting of Double-Stranded DNA," *Proc Natl Acad Sci*, 96(21):11804-11808 (1999).

Lukeman P.S., et al., "Two Dimensional PNA/DNA Arrays: Estimating the Helicity of Unusual Nucleic Acid Polymers," *Chem Commun*, 1694-1695 (2004).

Matsui M., et al. "Synthesis and Characterization of Mono-, Bis-, and Trissubstituted Pyridinium and Pyrylium Dyes," *Bull Chem Soc Jpn*, 65(1):71-74 (1992).

Matysiak, S., et al., "Automating Parallel Peptide Synthesis for the Production of PNA Library Arrays," *BioTechniques*, 31(4):896-904 (2001).

McRae, et al., "Enhancement of Phosphorescence Ability upon Aggregation of Dye Molecules," *M J of Chem Phys*, 28:721-722 (1958).

Mikheikin A.L., et al., "Binding of Symmetrical Cyanine Dyes into the DNA Minor Groove," *J. Biomol. Struct. Dyn.*, 18(1):59-72 (2000).

Møllegaard, N.E., et al., "Quinoxaline Antibiotics Enhanced Peptide Nucleic Acid Binding to Double-Stranded DNA," *Biochemistry*, 39(31):9502-9507 (2000).

Mulliken, R.S., "Interpretation of the Atmospheric Oxygen Bands; Electronic Levels of the Oxygen Molecule," *Nature*, 122: 505 (1928).

Mullis, et al., PCR: The Polymerase Chain Reaction (1994).

Nielsen P.E., et al., "Sequence-Selective Recognition of DNA by Strand Displacement with a Thymine-Substituted Polyamide," *Science*, 254:1497-1500 (1991).

Nulf, C. J., et al., Intraceullar Inhibition of Hepatitis C Virus (HCV) Internal Ribosomal Entry Site (IRES)-Dependent Translation by Peptide Nucleic Acids (PNAs) and Locked Nucleic Acids (LNAs), *Nucleic Acids Res.*, 32(13):3792-3798 (2004).

Orum H., et al., "Single Base Pair Mutation Analysis by PNA Directed PCR Clamping," *Acids Res.*, 21(23): 5332-5336 (1993).

Petersen M. and Wengel J., "LNA: a Versatile Tool for Therapeutics and Genomics," *Trends in Biotechnology*, 21(2):74-81 (2003).

Renikuntla B.R., et al., "Improved Photostability and Fluorescence Properties through Polyfluorination of a Cyanine Dye," *Org. Lett.*, 6(6):909-912 (2004).

Rye, H.S., et al., "Interaction of Dimeric Intercalating Dyes with Single-Stranded DNA," *Nucleic Acids Res.*, 23(7):1215-1222 (1995).

Sambrook et al., Molecular Cloning: A Laboratory Manual (2d ed., Cold Spring Harbor Press) (2000).

Santos P.F., et al., "Efficiency of Singlet Oxygen Generation of Aminosquarylim Cyanines," *J. Photochem. Photobiol. A: Chem.*, 163:267-269 (2004).

Seifert J.L., et al., "Spontaneous Assembly of Helical Cyanine Dye Aggregates on DNA Nanotemplates," *J. Am. Chem. Soc.*, 121(13): 2987-2995 (1999).

Sforza, S., et al., "Unconventional Method Based on Circular Dichroism to Detect Peanut DNA in Food by Means of a PNA Probe and a Cyanine Dye," *Chirality*, 17:515-521 (2005).

Soh, N., "Recent Advances in Fluorescent Probes for the Detection of Reactive Oxygen Species," Anal Bioanal Chem 386:532-543 (2006).

Smith J., et al., "Molecular Recognition of PNA-Containing Hybrids: Spontaneous Assembly of Helical Cyanine Dye Aggregates on PNA Templates," *J. Am. Chem. Soc.*, 121: 2686-2695 (1999).

Smolina, I., et al., "End Invasion of Peptide Nucleic Acids (PNAs) with Mixed-Based Composition with Linear DNA Duplexes," *Nucleic Acids Res.*, 33(17):e146 (2005).

Tomac, S., et al., "Ionic Effects on the Stability and Conformation of Peptide Nucleic Acid Complexes," *J. Am. Chem. Soc.* , 118:5544-5552 (1996).

Waggoner A., "Fluorescent Labels for Proteomics and Genomics," Curr. Opin. Chem. Biol., 10:62-66 (2006).

Wagner, J.R., et al., "Endogenous Oxidative Damages of Deoxycytidine in DNA," *Proc. Natl Acad Sci. USA*, 89:3380-3384 (1992).

Wang, M. et al., "Colorimetric Detection of PNA-DNA Hybridization Using Cyanine Dyes," *Methods Mol. Biol.*, 208:131-142 (2002).

Wang, M., et al., "Electrostatic Contributions to Cyanine Dye Aggregation on Peptide Nucleic Acid Templates," *Langmuir*, 19:6449-6455 (2003).

Weiler, J., "Hybridisation Based DNA Screening on Peptide Nucleic Acid (PNA) Oligomer Arrays," *Nucleic Acids Res.*, 25(14):2792-2799 (1997).

Weir, D.M. "Handbook of Experimental Immunology, vol. I: Immunochemistry" Fourth ed. (1986).

Wemmer D.E., "Designed Sequence-Specific Minor Groove Ligands," *Annu. Rev. Biophys. Biomol. Strut*, 29:439-461 (2000).

West, W., et al., "The Dimeric State of Cyanine Dyes," *J. Phys. Chem.*, 69:1894-1903 (1965).

Wilhelmsson, L., et al., "Genetic Screening Using the Colour Change of a PNA-DNA Hybrid-Binding Cyanine Dye," *Nucleic Acids Res.*, 30(2e3), 4 pgs. (2002).

Wittung, P., et al., "Interactions of DNA Binding Ligands with PNA-DNA Hybrids," *Nucleic Acids Res.*, 22(24):5371-5377 (1994).

Yarmoluk , S., "Interaction of Cyanine Dyes with Nucleic Acids. XXI. Arguments for Half-Intercalation Model of Interaction," *Biopolymers*, 62(4):219-227 (2001).

Yin, J.L., et al., Real-Time Reverse Transcriptase-Polymerase Chain Reaction (RT-PCR) For Measurement of Cytokine and Growth Factor mRNA Expression with Fluorogenic Probes or SYBR Green I, *Immunol. Cell Biol*, 79:213-21 (2001).

Zhang G., et al., "A Selective and Sensitive Chemiluminescence Reaction of 4,4'(5')-bis[2-(9-anthryloxy)ehtylthio]tetrathiafulvalene with Singlet Oxygen," *Chem Comm*, 2072-2073 (2004).

Zipper, H., "Investigations on DNA Intercalation and Surface Binding by SYBR Green I, Its Structure Determination and Methodological Implications," *Nucleic Acids Res.*, 32(12):e103 (2004).

Supplementary European Search Report for European Patent Application No. 07751566.6 dated Mar. 11, 2010.

* cited by examiner

SEQUENCE LISTING

<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: PNA sequence, TB23

<400> SEQUENCE: 1
gttttgggtc tgacgac                                          17

<210> SEQ ID NO 2
<211> LENGTH: 17
<212> TYPE: DNA
<213> ORGANISM: Artificial Sequence
<220> FEATURE:
<223> OTHER INFORMATION: PNA sequence, TB14

<400> SEQUENCE: 2
gtcgtcagac ccaaaac                                                  17

<210> SEQ ID NO 3
<211> LENGTH: 17
<212> TYPE: DNA
<213> ORGANISM: Artificial Sequence
<220> FEATURE:
<223> OTHER INFORMATION: PNA sequence, TB19

<400> SEQUENCE: 3
tgaaccgccc cggcatg                                                  17

<210> SEQ ID NO 4
<211> LENGTH: 17
<212> TYPE: DNA
<213> ORGANISM: Artificial Sequence
<220> FEATURE:
<223> OTHER INFORMATION: PNA sequence, TB15

<400> SEQUENCE: 4
accaagtaga cgggcga                                                  17

<210> SEQ ID NO 5
<211> LENGTH: 17
<212> TYPE: DNA
<213> ORGANISM: Artificial Sequence
<220> FEATURE:
<223> OTHER INFORMATION: PNA sequence, TB20

<400> SEQUENCE: 5
catccaaccg tcggtcg                                                  17

<210> SEQ ID NO 6
<211> LENGTH: 17
<212> TYPE: DNA
<213> ORGANISM: Artificial Sequence
<220> FEATURE:
<223> OTHER INFORMATION: DNA sequence complementary to TB14

<400> SEQUENCE: 6
gttttgggtc tgacgac                                                  17

<210> SEQ ID NO 7
<211> LENGTH: 17
<212> TYPE: DNA
<213> ORGANISM: Artificial Sequence
<220> FEATURE:
<223> OTHER INFORMATION: DNA sequence complementary to TB19

<400> SEQUENCE: 7
catgccgggg cggttca                                                  17

<210> SEQ ID NO 8
<211> LENGTH: 17
<212> TYPE: DNA
<213> ORGANISM: Artificial Sequence
<220> FEATURE:
<223> OTHER INFORMATION: DNA sequence complementary to TB15

<400> SEQUENCE: 8
tcgcccgtct acttggt                                                  17

```
<210> SEQ ID NO 9
<211> LENGTH: 17
<212> TYPE: DNA
<213> ORGANISM: Artificial Sequence
<220> FEATURE:
<223> OTHER INFORMATION: DNA sequence complementary to TB20

<400> SEQUENCE: 9
cgaccgacgg ttggatg                                              17

<210> SEQ ID NO 10
<211> LENGTH: 17
<212> TYPE: DNA
<213> ORGANISM: Artificial Sequence
<220> FEATURE:
<223> OTHER INFORMATION: DNA sequence complementary to TB23

<400> SEQUENCE: 10
gtcgtcagac ccaaaac                                              17
```

ASSAYS BASED ON DETECTION OF PHOTOBLEACHING REACTION PRODUCTS FROM DYE CATALYTIC COMPLEX

FEDERALLY SPONSORED RESEARCH OR DEVELOPMENT

This research was supported in part by Grant Numbers R43AI069574 and R44AI069574 from the National Institute of Allergy and Infectious Diseases.

REFERENCE TO APPENDIX

Attached hereto is a sequence listing as part of this application.

BACKGROUND

Peptide nucleic acids (PNAs) are nucleic acid analogs where the negatively charged phosphoribose backbone has been replaced with a neutral N-(2-aminoethyl) glycine group[1-2]. The absence of the negatively charged backbone gives PNAs unique physiochemical properties for binding to nucleic acid targets. PNAs rapidly hybridize to single-stranded DNA or RNA[3-4] and PNA-DNA or PNA-RNA duplexes have much higher thermal stability than the corresponding DNA-DNA or DNA-RNA duplexes. The melting temperature ($T_m$) of a PNA-DNA duplex is relatively insensitive to ionic strength, and shows equal thermal stability under low (10 mM) and moderate (500 mM) salt concentrations[2, 5]. PNA-DNA hybridization is severely affected by base mismatches. A single base pair mismatch destabilizes a PNA-DNA duplex to a greater extent than a mismatch in a DNA-DNA duplex[2]. These properties give PNA probes many advantages over conventional DNA probes. The exceptional characteristics of PNA probes are the basis for the development of several technologies such as PNA arrays[6, 7], antisense DNA targeting[8, 9], nucleic acid purification[10], and mutation analysis[11].

Designing assays that require PNA invasion of duplex DNA, however, remains difficult. Typically these assays benefit from PNA backbone modification[12], conjugation "scanning" peptides[13], specific structural features of the target DNA, and overnight incubation with elevated temperature such as 55° C.[3, 12, 14, 15]. These requirements seriously impact the efficient application of PNAs to routine diagnostic product development.

The non-covalent interactions of small molecules, including sequence-specific DNA binding polyamides[16] and cyanine dyes[17] with DNA duplexes have been widely reported. Binding modes of cyanine dyes to DNA duplexes include electrostatic interactions of the cationic dye with the anionic phosphodiester groups of the nucleic acid[18, 19], intercalation between base pairs[20], hydrophobic-associated interactions within the minor groove[21, 22], and half-intercalation models[23]. Cyanine dyes have been used in many different applications including detection of DNA and RNA in agarose gels[24], fluorescent labels in cellular imaging[25], sequence-specific DNA detection using cyanine dye-conjugated DNA oligonucleotide molecular beacons[26], and real-time PCR[27]. The potential utility of cyanine dyes in nucleic acid detection has been improved by enhancing the fluorescence intensity of nucleic acid bound dye relative to unbound (free) dye[28] or chemically modifying the light-sensitive cyanine dyes to be more resistant to photobleaching[29, 30].

While most traditional double-stranded DNA binding ligands do not bind PNA-DNA duplexes[31], the cyanine dye, 3,3'-diethylthiadicarbocyanine iodide ($DiSC_2(5)$), does bind to PNA-DNA duplexes[32,-35]. $DiSC_2(5)$ and a closely related cyanine dye, $DiSC_{3-}(5)$, form aggregates in the minor groove of PNA-DNA oligomer duplexes[35]. This aggregate formation results in an approximate 114 nm absorbance shift (blue to violet) that can be observed by eye[32]. Furthermore, the UV-vis spectra of $DiSC_2(3)$ with the random PNA-DNA 10 base pairs duplex was scanned. An attenuated/broadened spectrum was observed and was regarded as indicating a lack of a well-defined complex of $DiSC_2(3)$ aggregation on the PNA-DNA duplex but was not further investigated[32].

Photobleaching of cyanine dyes is usually seen as an undesirable characteristic which hampers their use in nucleic acid detection. However, in the presence of a target specific peptide nucleic acid (PNA) oligomer probe, the rate of 3,3'-diethylthiacarbocyanine iodide ($DiSC_2(3)$) photobleaching is directly related to the amount of target DNA present. This type of reaction is referred to herein as "smartDNA™" and this rapid color loss can be used as sensitive indicator for the presence of, absence of and/or amount of a specific DNA sequence.

Under certain conditions, when $DiSC_2(3)$ is mixed with a PNA-DNA duplex, the mixture has a rapid color change (photobleaching of the original pink color of the dye). For example, when a complementary PNA probe, a DNA target, and the cyanine dye $DiSC_2(3)$ are combined and exposed to 470 nm light, a rapid sequence-specific accelerated photobleaching reaction occurs. UV-vis, Circular Dichroism (CD) and fluorescence spectroscopy can be used to examine the interaction of $DiSC_2(3)$ and related dyes with PNA-DNA oligomer duplexes. This accelerated photobleaching reaction is rapid and the rate is directly related to the DNA target concentration in the sample. The extent of the color loss can be estimated by eye or measured with a simple photometer which allows sensitive DNA measurements to be performed on genomic DNA samples with minimal hardware. Thus, the utility of high affinity PNA-DNA binding is further improved by the discovery of the color loss reaction and a rapid room temperature binding process that occurs in the presence of $DiSC_2(3)$ and related dyes. As mentioned above, this PNA-dye-light mediated method of detecting DNA is called "smartDNA™" and the assays developed with this rapid easy method may have wide utility including infectious disease diagnostics, genotyping, monitoring, environmental, industrial and agricultural applications.

SUMMARY

The present invention relates to Applicant's discovery that the accelerated photobleaching of dye after exposure of a nucleic acid analog/nucleic acid analog binding substrate/dye complex to light operates by a mechanism that involves formation of singlet oxygen and/or other reaction products of the novel catalytic complex (dye, nucleic acid analog and nucleic acid analog binding substrate). Thus, the invention relates to methods for assaying a nucleic acid analog binding substrate in a sample, comprising reacting a catalytic complex comprising a nucleic acid analog, a nucleic acid analog specific binding substrate and a light reactive dye with a light stimulus, and detecting (directly or indirectly) the presence or absence or amount of a reaction product, such as e.g., singlet oxygen or other reaction product(s) of the catalytic complex and light stimulus. Any of the reaction products may be detected by methods that are independent of the direct measurement of the change in color due to breakdown of the dye substrate when that dye substrate also functions as part of the catalytic complex.

For example, the presence of singlet oxygen may be measured directly or indirectly. The presence of single oxygen can be determined by methods including, but not limited to, measurement of the singlet oxygen infrared emission (phosphorescence) at about 1270 nm (Khan and Kasha, 1979) (or time-resolved singlet oxygen phosphorescence detection either by analog or photon counting (Jimenez-Banzo et al., 2008), the fluorescence of the singlet oxygen dimol at about 634 nm (Mulliken, 1928), measuring the generation of stable nitroxide radicals from sterically hindered amines (Lion et al., 1976), electron spin resonance, calorimetry, photo ionization, mass spectroscopy, alteration of scavengers, altered reactions in the presence of D2O, increased fluorescence of singlet oxygen sensor molecule, such as sensor green (Invitrogen), DPAX or DMAX (Gomes et al., 2005) decreased fluorescence of a singlet oxygen sensor molecule, such as DMA (Gomes et al., 2005) or sensors for detecting singlet oxygen and superoxide production such as DanePy and HO-2941 (Barta et al., 2002), time resolved luminescence detection of singlet oxygen with ATT-Eu3+ (Gomes et al., 2005), fluorescence enhancement and/or chemiluminescence produced by the interaction of singlet oxygen with anthracene skeleton of 4,4'(5')-bis[2-(9-anthryloxy)ethylthio]tetrathiafulvalene (Zhang et al., 2004; Soh, 2006) or using any other singlet oxygen sensor molecule or singlet oxygen sensitive detector molecule. The terms "singlet oxygen sensor molecule" or "singlet oxygen sensitive detector molecule" refer to a molecule (e.g., singlet oxygen sensitive dye) that is capable of interacting with the singlet oxygen, and/or any other molecule(s) that react with the singlet oxygen, in a detectable manner, such as DPAX, DMAX, ATTA-Eu3+ and 4,4'(5')-bis[2-(9-anthryloxy)ethylthio]tetrathiafulvalene, except cyanine dyes.

In another embodiment, the invention contemplates use of a reporter complex for detecting the presence or absence of an analyte. The reporter complex comprises a nucleic acid analog binding substrate (to which the nucleic acid analog and dye bind to form the catalytic complex) linked to an analyte binding component, such as an antibody, which binds directly to the analyte. As indicated previously, detection of the analyte may be accomplished by directly or indirectly detecting or measuring the amount of singlet oxygen or any other primary or secondary reaction products produced by the catalytic complex or the singlet oxygen.

Specifically, in one embodiment, the invention contemplates a method for assaying an analyte in a sample. The method includes mixing the sample with a reporter molecule or components thereof comprising a nucleic acid analog, a nucleic acid analog binding substrate that is complementary to the nucleic acid analog, and a dye, wherein the components of the reporter molecule form a catalytic complex. One of the nucleic acid analog or the nucleic acid analog binding substrate components of the reporter molecule is bound to an analyte specific binding compound and the analyte, if present in the sample, binds to the analyte specific binding compound. The method also includes removing from the mixture any reporter molecule not bound to the analyte, exposing the mixture to light stimulus, and detecting the presence or absence or amount of a reaction product of the catalytic complex and light stimulus.

TABLE 1

| SEQ ID NO: | PNA | sequence | SEQ ID No: | DNA sequence |
|---|---|---|---|---|
| 2 | TB14 (gel lane 1) | GTCGTCAGACCCAAAAC | 6 | GTTTTGGGTCTGACGAC |
| 3 | TB19 (gel lane 2) | TGAACCGCCCCGGCATG | 7 | CATGCCGGGGCGGTTCA |
| 4 | TB15 (gel lane 3) | ACCAAGTAGACGGGCGA | 8 | TCGCCCGTCTACTTGGT |
| 5 | TB20 (gel lane 4) | CATCCAACCGTCGGTCG | 9 | CGACCGACGGTTGGATG |
| 1 | TB23 | GTTTTGGGTCTGACGAC | 10 | GTCGTCAGACCCAAAAC |

PNA names and sequences. All PNAs have a C-terminal carboxamide. The modification on the N-terminal is Lysine.

Figure 3:
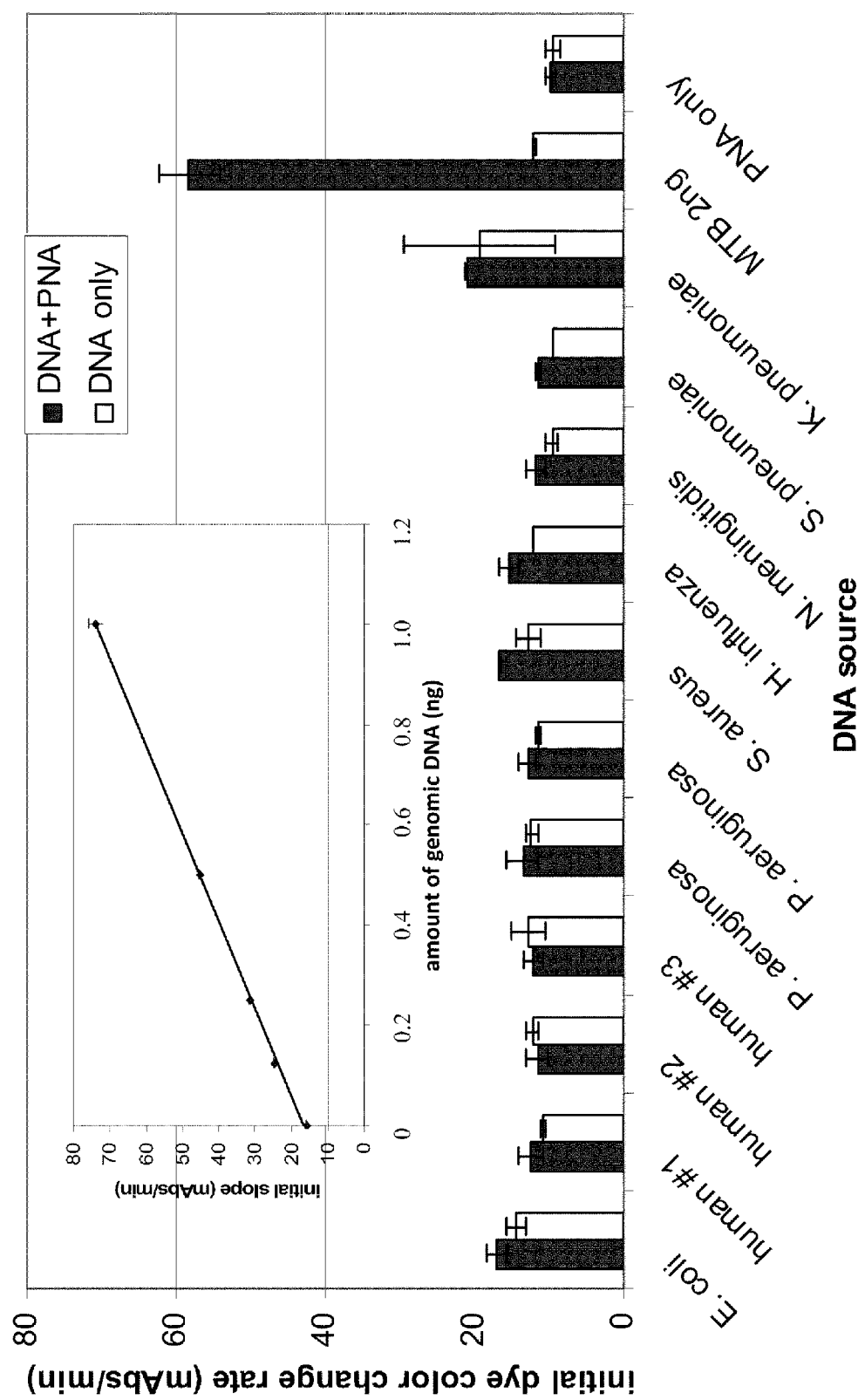

FIG. 3 is a graph illustrating the initial (first 4 minutes) photobleaching rate of smartDNA reactions with 2 ng DNA from *M. tuberculosis* (MTB) or from non-*M. tuberculosis* species in the presence and absence of *M. tuberculosis* specific PNA probe. The reaction was performed in 10 mM Homopipes buffer, pH5.0, with 0.05% Tween-80, and PNA probe used was TB19, the final concentration of PNA in the 50 µl reaction is 160 nM. The inlay shows dose response curve of TB14 against *M. tuberculosis* genomic DNA. The photobleaching rate (milliAbsorbance units/min) was calculated for each genomic DNA concentration and plotted.

Figure 4:
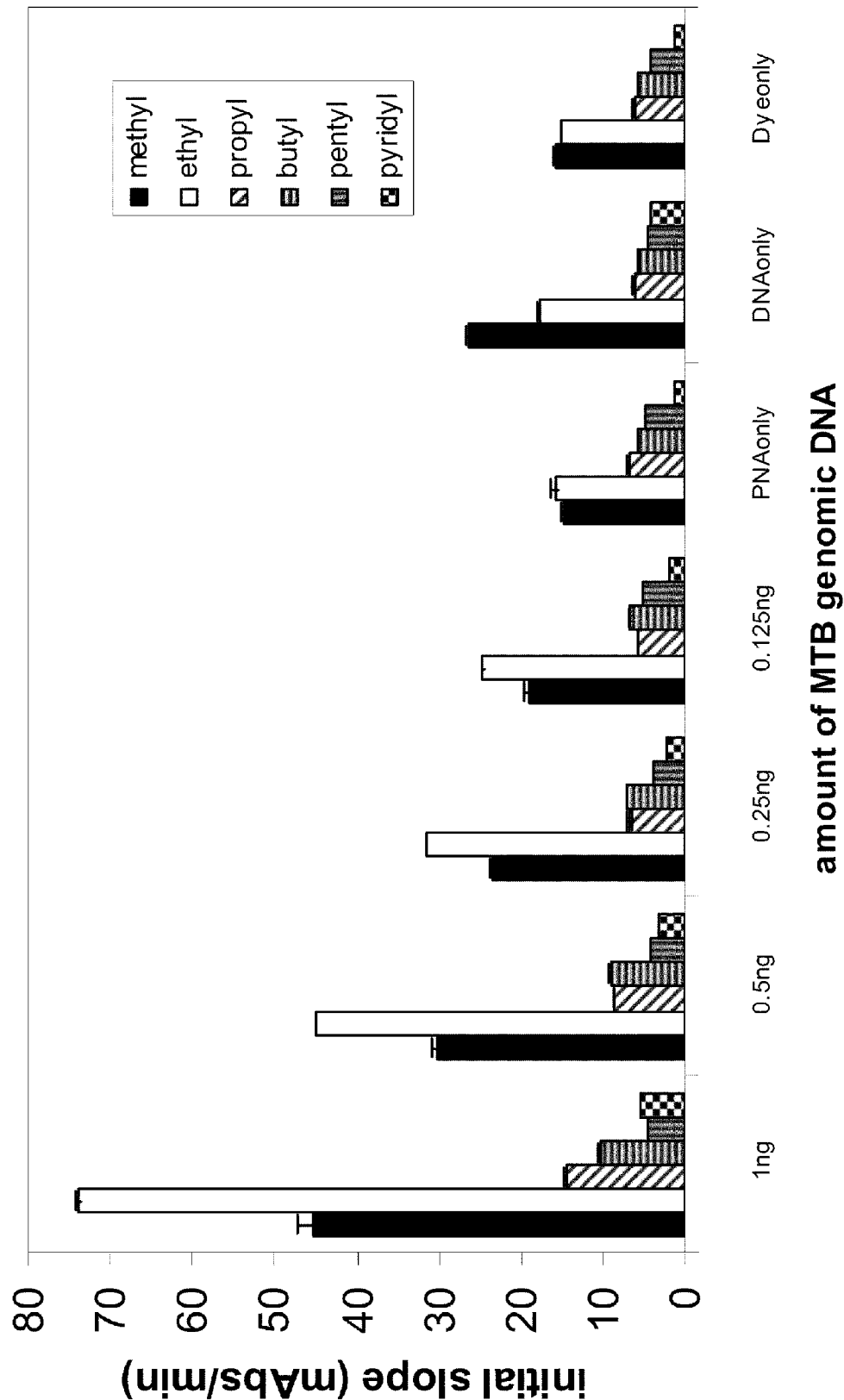

FIG. 4 is a graph illustrating comparison of the photobleaching rate of the thiacarbocyanine dyes with substituents of ethyl, propyl, butyl, pentyl and pyridinium, (corresponding to $DiSC_2(3)$, $DiSC_3(3)$, $DiSC_4(3)$, $DiSC_5(3)$, and $DiSC_{py}(3)$, respectively). Structure of these dyes are shown in the inlay of the plot, with the left structure, n=1 for $DiSC_2(3)$, n=2 for $DiSC_3(3)$, n=3, for $DiSC_4(3)$, n=4 for $DiSC_5(3)$, and the right structure is $DiSC_{py}(3)$. Label on X-axis shows the amount of *M. tuberculosis* (MTB) genomic DNA in each reaction. PNA probe used here is TB14, sequence shown in Table 1. The final concentration of PNA in the 50 µl reaction is 160 nM. All dyes had final concentration of 9 µM. The buffer is 10 mM Homopipes, pH 5.0, 0.05% Tween 80.

Figure 5:
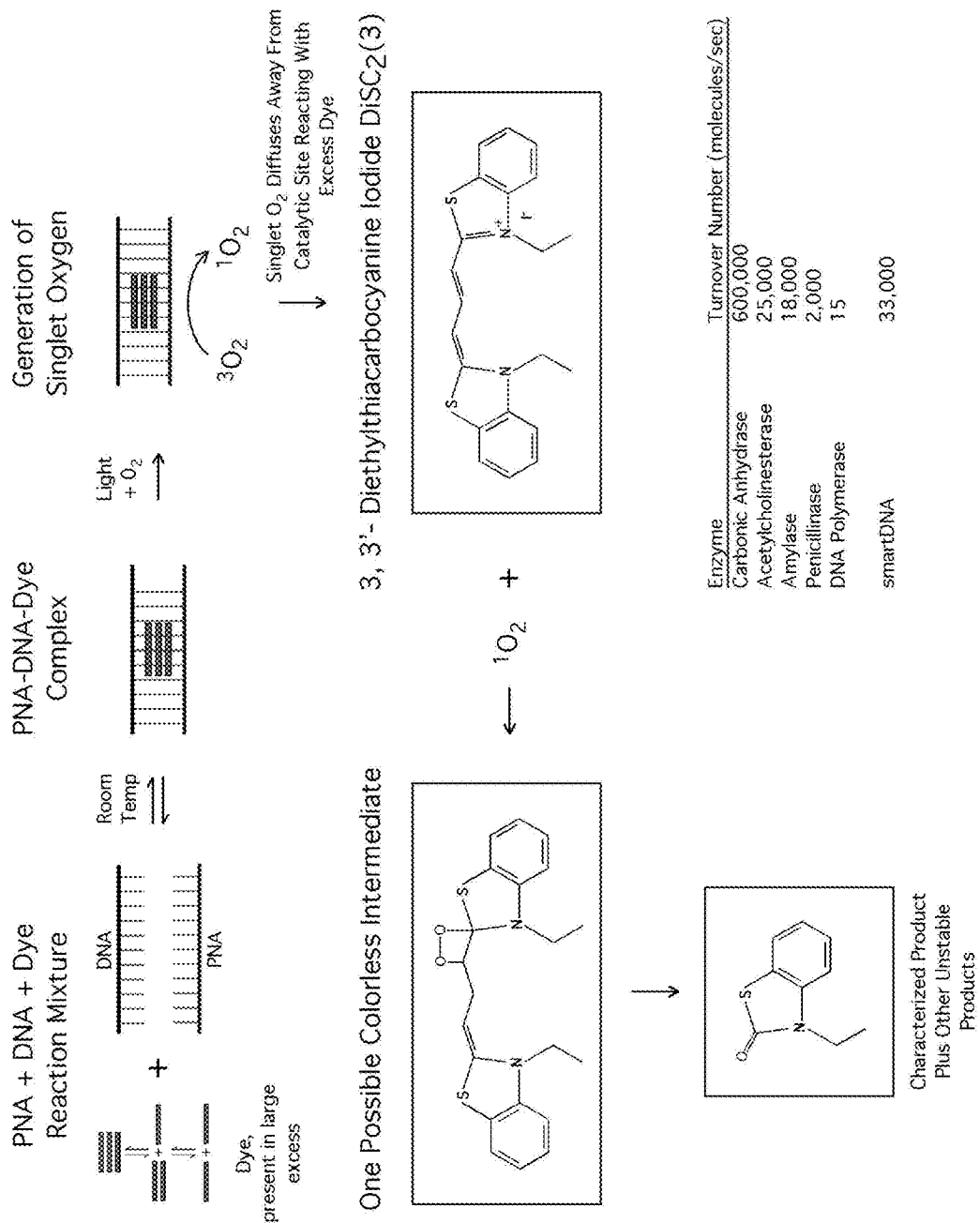

FIG. 5 depicts a proposed mechanism of accelerated photobleaching based on the generation of singlet oxygen.

Figure 6:
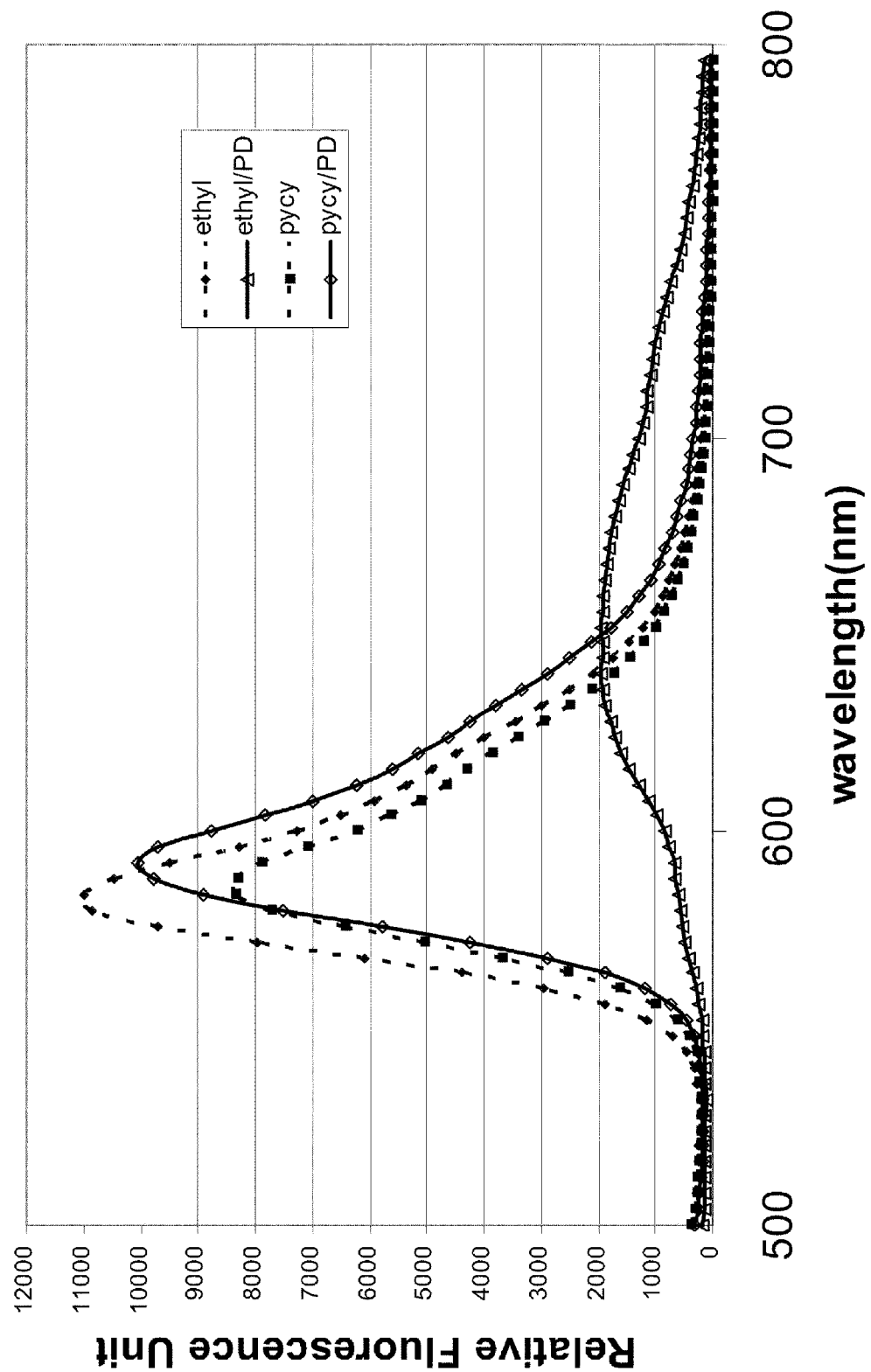

FIG. 6 depicts the fluorescence emission spectra of 2.25 uM $DiSC_2(3)$ or $DiSC_{py}(3)$, alone or with 0.25 µM PNA-DNA duplex. PNA TB23 was used, the reactions were in 10 mM Homopipes buffer, pH 5 and 470 nm was the excitation wavelength.

Figure 7:
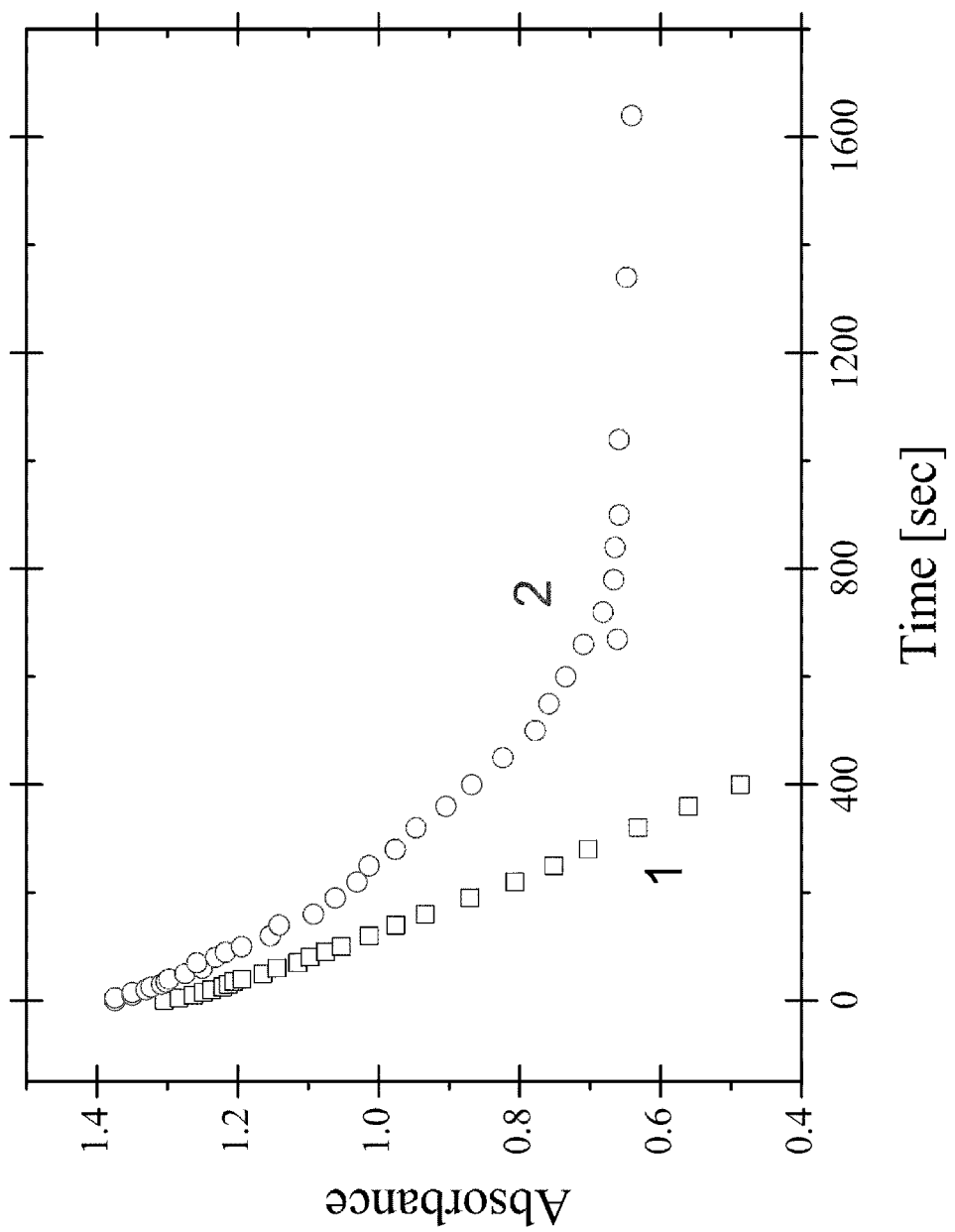

FIG. 7 depicts the effects of oxygen presence on the absorbance maxima of $DiSC_2(3)$. The changes of the absorption intensity at $\lambda_{max}$ during irradiation of $DiSC_2(3)$ in phosphate buffer solution in: 1 oxygen saturated solution and 2 in argon saturated solution. Time of argon bubbling was 100 minutes.

Figure 8:
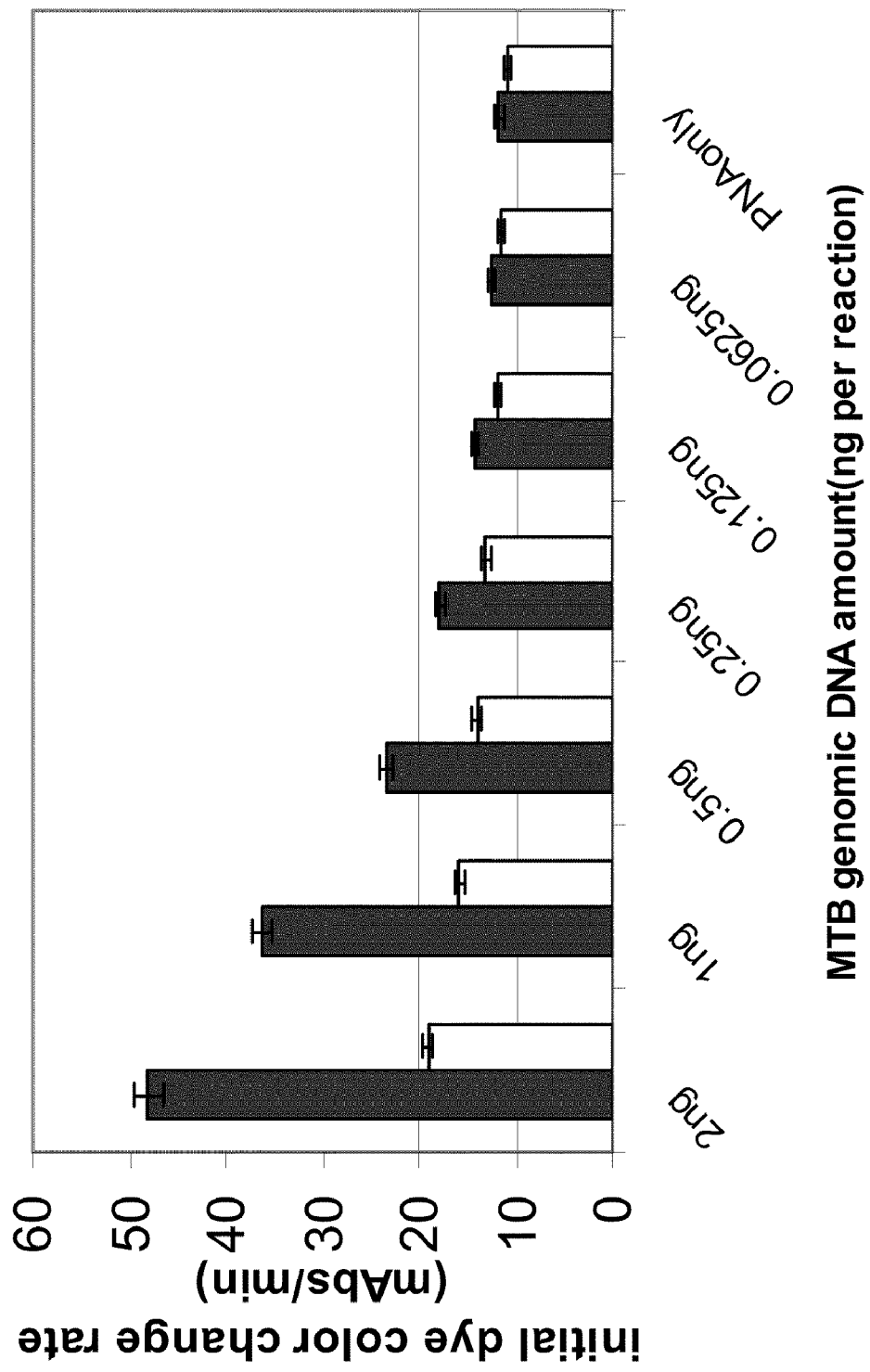
Figure 9:
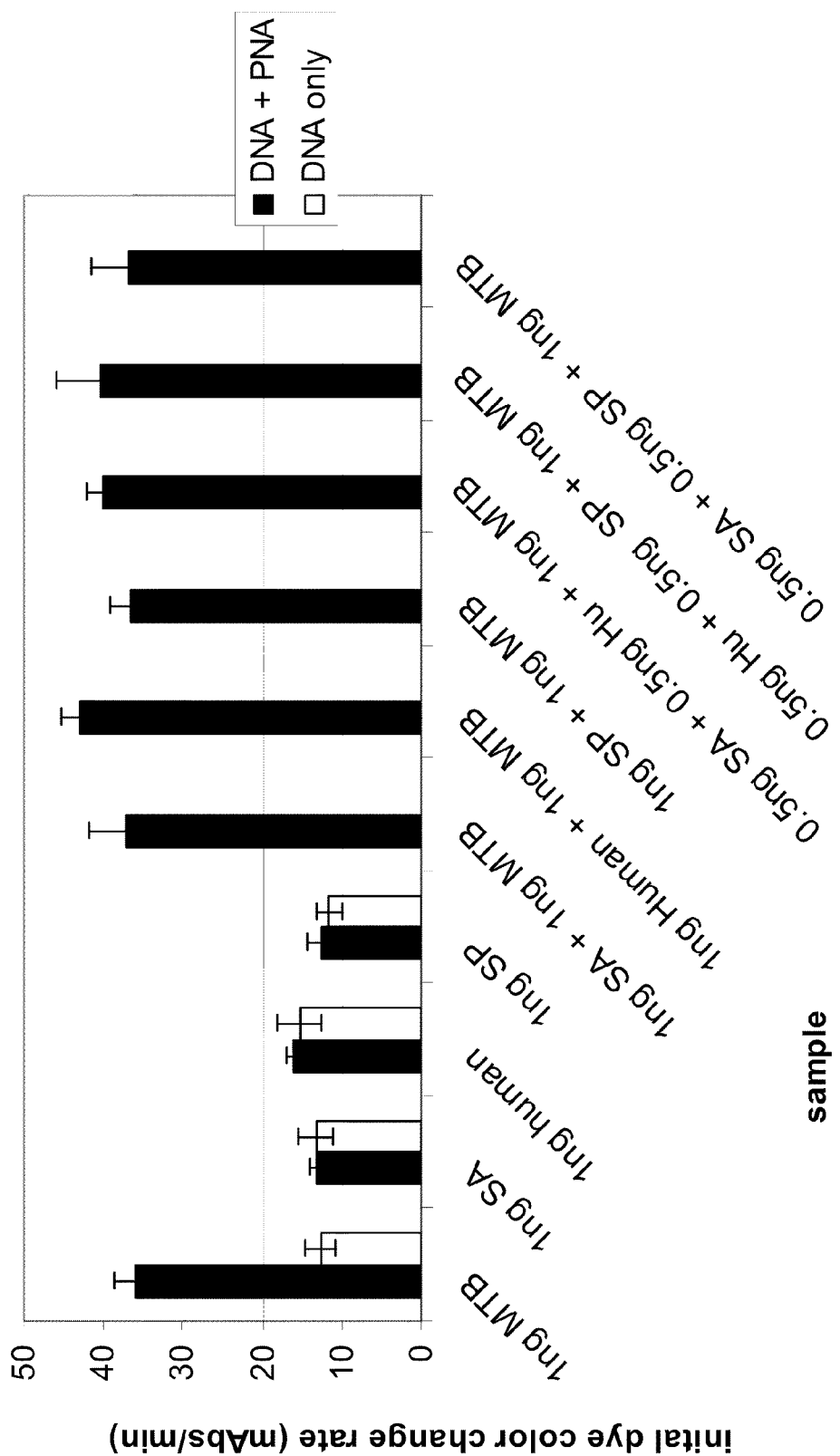

FIG. 8 depicts the effects of sodium azide on a smartDNA assay. The final concentration of the PNA probe, TB01, is 80 nM, and of $DiSC_2(3)$ is 9 µM, with 2 ng of *M. tuberculosis* (MTB) genomic DNA. The black bars are initial photobleaching rates in Homopipes buffer, pH 5.0, 10 mM, and the white bars are the initial photobleaching rate in the presence of 0.1% sodium azide FIG. 9 depicts the detection of MTB DNA in the presence of non-specific DNA. The initial (first 4 minutes) photobleaching rate of smartDNA reactions with *M. tuberculosis* (MTB) DNA alone, non-*M. tuberculosis* species DNA alone, and mixtures of DNA in the presence and absence of *M. tuberculosis* specific PNA probe, TB19. Reaction conditions are 10 mM Homopipes buffer, pH5.0, with 0.05% Tween-80, the final concentration of PNA in the 50 µl reaction is 160 nM. "SP" is *Streptococcus pneumoniae* DNA. "SA" is *Staphylococcus aureus* DNA. "Hu" is Human DNA.

DETAILED DESCRIPTION

The present invention provides methods for assaying a nucleic acid analog binding substrate in a sample, comprising reacting a catalytic complex comprising a nucleic acid analog, a nucleic acid analog specific binding substrate and a light reactive dye with a light stimulus, and detecting (directly or indirectly) the presence or absence or amount of a reaction product produced by the catalytic complex upon exposure to light. In particular, the present invention relates to methods of detecting and measuring singlet oxygen produced by the catalytic complex. The present invention also relates to the use of the catalytic complex as a reporter complex to produce singlet oxygen, which can be used to detect other target molecules (i.e., analytes) to which the reporter complex binds.

In many settings, molecular testing is needed but unavailable due to complexity and cost. Simple, rapid and specific DNA detection technologies would provide important alternatives to existing detection methods. The present invention provides a rapid nucleic acid detection method based on the accelerated production of singlet oxygen in the presence of a nucleic acid binding substrate and a complementary nucleic acid analog, such as a peptide nucleic acid (PNA) probe.

Based on the UV-vis, Circular Dichroism, and fluorescence spectra of $DiSC_2(3)$ with PNA-DNA oligomer duplexes and on characterization of a product of photolysis of $DiSC_2(3)$ I$^-$, the evidence indicates that (1) a novel complex forms between dye, nucleic acid analog (e.g. PNA) and a nucleic acid analog binding substrate, (2) this complex functions as a photosensitizer producing $^1O_2$ and/or other reaction products, and (3) the resulting $^1O_2$ can be detected and measured directly, or indirectly by detecting and measuring reaction products of the $^1O_2$ with other chemicals, and then correlated with the presence, absence, or amount of the analyte of interest, if present in the sample. Similar cyanine dyes ($DiSC_3(3)$, $DiSC_4(3)$, $DiSC_5(3)$, and $DiSC_{py}(3)$) interact with pre-formed PNA-DNA oligomer duplexes. While some effect is observed, under the conditions tested these dyes do not demonstrate an equivalent accelerated photobleaching effect in the presence of PNA and target genomic DNA. Molecular diagnostic assays may utilize the accelerated photobleaching (the smartDNA assay) that results from the novel complex formed between $DiSC_2(3)$ and PNA-DNA as a basis for detecting the presence or absence of and quantifying analytes in a sample.

General Techniques

The practice of the present invention employs, unless otherwise indicated, conventional techniques of molecular biology (including recombinant techniques), microbiology, cell biology, chemistry, biochemistry, immunology, protein kinetics, and spectroscopy, which are within the skill of the art. Such techniques are explained fully in the literature, such as, Sambrook et al., MOLECULAR CLONING: A LABORATORY MANUAL (2d ed., Cold Spring Harbor Press 2000); CELL BIOLOGY: A LABORATORY NOTEBOOK (J. E. Cellis, ed., Academic Press 1998); ANIMAL CELL CULTURE (R. I. Freshney, ed., 1987); METHODS IN ENZYMOLOGY (a series of volumes directed at enzymology protocols that is published by Academic Press, Inc.); HANDBOOK OF EXPERIMENTAL IMMUNOLOGY (D. M. Weir and C. C. Blackwell, eds.); PCR: THE POLYMERASE CHAIN REACTION (Mullis et al., eds., 1994); and the like. Furthermore, procedures employing commercially available assay kits and reagents typically are used according to manufacturer-defined protocols, unless otherwise noted.

Definitions

The term "analyte" generally refers to a target molecule(s) that is detected using the methods or complexes disclosed herein. The analyte can be a DNA analyte, an RNA analyte, a nucleic acid analyte, macromolecule or a small molecule as those terms are used in the art. In particular, a macromolecule may include, for example, a polynucleotide, a polypeptide, a carbohydrate, a lipid, or a combination of one or more of these. As a general rule, the molecular mass of a macromolecule is at least about 300 Daltons and can be millions of Daltons. A small molecule is an organic compound having a molecular weight of up to about 300 Daltons. In certain instances, the analyte is a nucleic acid analyte.

The terms "nucleic acid analog binding substrate" or "binding substrate" mean a molecule to which the nucleic acid analog is capable of specifically binding and forming a catalytic complex with the dye. The binding substrate may be the nucleic acid analyte that is being detected, or, alternatively, may be a nucleic acid component of a reporter molecule, a different portion of which specifically binds to the analyte. Thus, an "analyte comprising a nucleic acid analog binding substrate" encompasses both a nucleic acid analog binding substrate that is the analyte itself, as well an analyte that is bound to a nucleic acid analog binding substrate by means of intermediate bridging molecule(s), such as an analyte specific binding molecule that is bound to the nucleic acid analog binding substrate. For example, the nucleic acid analog binding substrate may be a nucleic acid molecule that is bound to an antibody that specifically binds a protein analyte of interest. The nucleic acid analog binding substrate may also be a nucleic acid molecule that is bound to an antigen that specifically binds to an antibody analyte of interest. Thus, the nucleic acid analog binding substrate may be bound, either directly or indirectly, to any molecule that specifically binds to the analyte of interest. The nucleic acid analog binding substrate may also be another nucleic acid analog. Alternatively, the nucleic acid analog may be bound to an intermediate bridging molecule(s), such as analyte specific binding molecule.

The term "analyte binding component" refers to a molecule or any part thereof that is capable of directly binding with the analyte. In one instance, the analyte binding component may be an antibody.

The term "nucleic acid analyte" refers to an analyte that comprises a polynucleotide, at least a portion of which is capable of functioning as the binding substrate for the nucleic acid analog and a dye, to form the catalytic complex. Some mismatch may exist depending on the conditions of the reaction mixture. The binding could be by way of Watson-Crick hybridization, a modified Watson-Crick hybridization, or sequence specific binding modes yet undescribed. The nucleic acid analyte may be of any length. In many instances, the nucleic acid analyte can be greater than 40,000 base pairs long. In some diagnostic applications, however, the nucleic acid analyte is the product of PCR amplification of genomic DNA, which is typically less than about 1000 bases. The analytic nucleic acid sequence may, of course, be less than about 500 bases, less than about 100 bases, less than about 40 bases, or less than about 24 bases. In other embodiments, the nucleic acid analyte may be greater than about 4, about 5, about 6, about 7, about 8, about 9, about 10, about 12, about 14, about 16, about 18, about 20, about 25, about 30, about 35, about 40, about 45, or about 50 bases in length. In yet other embodiments, the nucleic acid analyte is preferably greater than about 4 bases and less than about 24 bases in length. In certain embodiments, the nucleic acid analyte is about 4, about 6, about 8, about 10, about 12, about 14, about 16, about 18, about 20, about 22, or about 24 bases in length. The nucleic acid analyte may include a protein coding sequence and/or a non-coding sequence (e.g., intergenic spacer sequences regulatory sequences, introns, non-coding RNA and the like).

The term "polynucleotide" refers to a polymeric form of nucleotides or nucleotide analogs of any length, either deoxyribonucleotides or ribonucleotides, or analogs thereof, or mixtures thereof. Polynucleotides may be single-stranded, double-stranded, triple-stranded, or multi-stranded to yet greater degrees. The following are non-limiting examples of polynucleotides: a gene or gene fragment, exons, introns, messenger RNA (mRNA), transfer RNA, ribosomal RNA, armored RNA, non-coding RNA, microRNA, ribozymes, cDNA, recombinant polynucleotides, branched polynucleotides, plasmids, vectors, nucleic acid probes, primers, amplified DNA, and synthesized DNA. A polynucleotide may contain modified bases, including those that include, without limitation, a methylation, deamination, thiolation, and/or acetylation. The sequence of nucleotides of a polynucleotide may be interrupted by non-nucleotide components, and may include one or more nucleic acid analogs. A polynucleotide may be further modified before or after polymerization, such as by conjugation with a labeling component. The polynucleotide may be an amplified region of a longer sequence of nucleotides. A polynucleotide may be a peptide nucleic acid (PNA), among other nucleic acid analogs.

The term "nucleic acid analog" refers to any molecule that is described in part by a sequence of bases, as is commonly done for DNA or RNA, which molecule has one or more bases that differ from conventional guanine, thymine, adenosine, cytosine, or uracil, and/or having one or more differences from the conventional phosphoribose of an RNA backbone or the conventional phosphodeoxyribose of a DNA backbone at one or more bases. Nucleic acid analogs can be chimeric by having a specific type of nucleic acid analog nucleoside in combination with another nucleic acid analog nucleoside, and/or one or more conventional DNA nucleosides or RNA nucleosides.

The nucleic acid analog may be an achiral peptide nucleic acid (referred to herein as any of "non-chiral PNA", "achiral PNA", or "ncPNA"), a chiral peptide nucleic acid (referred to herein as "chiral PNA" or "cPNA"), a locked nucleic acid ("LNA"), a threose nucleic acid ("TNA"), a metal-linked nucleic acid, or a morpholino nucleic acid. More preferably, the nucleic acid analog is a cPNA or a ncPNA.

The nucleic acid analog is preferably greater than about 4 bases in length and less than about 24 bases in length, excluding linkers, amino acids and labels. In other embodiments, the nucleic acid analog may be from about 5 to about 100, from about 8 to about 60, or from about 10 to about 20 bases in length. In another embodiment, the nucleic acid analog is about 6, about 8 about 10, about 12, about 14, about 18, about 22, about 26, about 30, about 35, about 40, or about 45 bases in length, excluding linkers, amino acids and labels. Preferably, the nucleic acid analog is about 12 nucleic acid bases in length. In another embodiment of the invention, the nucleic acid analog is about 17 or about 18 nucleic acid bases in length, however the method can be operated using a wide range of lengths of the nucleic acid analog.

The term "peptide nucleic acid," or "PNA," includes any nucleic acid analog in which the deoxyribose phosphate backbone of a nucleic acid has been replaced by a synthetic peptide-like backbone, including, for example, n-(2-aminoethyl)-glycine units, such as, without limitation, those disclosed in U.S. Pat. Nos. 5,786,461; 6,357,163; 6,107,470; 5,773,571; 6,441,130, 6,451,968; 6,228,982; 5,641,625; 5,766,855; 5,736,336; 5,719,262; 5,714,331; 5,719,262; and 6,414,112. The purine and pyrimidine bases may be attached by any covalent linkage, including, for example, methylene carbonyl linkages. As used herein, PNA molecules can have additional atoms between the PNA backbone and nucleobase. These analogs include, for example, D-lysine chains, cyclic structures, such as cyclopentane or pyrrolidine rings, and/or chiral substituents, including PNA molecules described in U.S. Pat. No. 6,403,763, U.S. Patent Application US 2003/0162699, and U.S. Patent Application US 2003/0157500. The PNA backbone may include substitutions or extensions in the peptide backbone. PNAs may include peptide-based nucleic acid mimics (PENAMS), such as those disclosed, for example, in U.S. Pat. No. 5,705,333, atoms having unusual chiral centers, such as D-chiral centers and quasi-chiral centers, and atom substitutions in the PNA backbone.

The term "chiral PNA" or "cPNA" refers to a chiral PNA molecule in which at least a portion of the peptide backbone has been modified to include a proline or modified proline side-chain that includes the backbone nitrogen and a-carbon. Non-limiting examples of chiral PNA molecules include those that are disclosed at, for example, U.S. Pat. No. 6,403, 763, U.S. Patent Applications US 2003/0162699 and US 2003/0157500.

The term "achiral PNA" or "non-chiral PNA" or "ncPNA" refers to a PNA molecule in which no portion of the peptide backbone has been modified to include a proline or modified proline side chain that includes the backbone nitrogen and α-carbon.

The term "non-PNA nucleic acid analog" refers to a nucleic acid analog in which the backbone does not include a synthetic peptide-like backbone.

The term "locked nucleic acid" or "LNA" refers to a bicyclic nucleic acid in which at least one ribonucleoside is linked between the 2'-oxygen and the 4'-carbon with a methylene group. Non-limiting examples of LNAs are disclosed in TRENDS IN BIOTECHNOLOGY 71:74-81 (2003).

The term "morpholino nucleic acid" or "MNA" refers to a nucleic acid analog in which each backbone monomer is a substituted or unsubstituted six-membered morpholino ring. The morpholino rings are linked by non-ionic phosphorodiamidate linkages. Non-limiting examples of MNAs include those described in U.S. Pat. 5,034,506.

The term "threose nucleic acid" or "TNA" refers to a nucleic acid in which the sugar-phosphate backbone is a four-carbon sugar threose in place of the five-carbon sugar ribose.

The term "photochemical reaction" refers to a reaction that can occur when electromagnetic radiation interacts with matter and initiates the production of new chemical species. Absorption of electromagnetic radiation, typically in the region of the electromagnetic spectrum which ranges from approximately 180 nanometers in the ultraviolet to 800 nanometers in the near infrared, initiate electronic transitions in the absorbing species and result in a temporary change in its electronic structure. This electronically excited species may reemit the energy absorbed via radiationless decay, fluorescent emission, or phosphorescent emission resulting in no change to the original absorber. Alternatively, the electronically activated species can undergo an irreversible electronic change creating a new product molecule or molecules. Also, the electronically excited species can interact with a second molecule with the same or different chemical structure in the sample causing changes in that molecule's electronic structure which in turn can cause reversible or irreversible changes to the second molecule. Products of these photochemically induced reactions can in turn react with other chemically distinct molecules in the sample to initiate other chemical reactions.

The terms "nucleic acid analog/nucleic acid analog binding substrate complex" or "nucleic acid analog/binding substrate complex" refers to a nucleic acid analog that is sufficiently complementary to its binding substrate so that it forms a sequence-specific complex. Non-limiting examples of nucleic acid analog/binding substrate complexes include nucleic acid analog/binding substrate complexes, duplexes and triplexes. The term "PNA/polynucleotide analyte complex" refers to a PNA molecule that is sufficiently complementary to a polynucleotide analyte to form a sequence-specific complex. Non-limiting examples of PNA/polynucleotide analyte complexes include PNA/polynucleotide duplexes and triplexes. The PNA may be chiral or non-chiral.

The term "complementary" means that a single-stranded nucleic acid analog has the ability to bind to a binding substrate in a sequence-specific manner. The nucleic acid analog may be synthesized to fully or partially bind to the binding substrate. A nucleic acid analog that is "complementary" may have one or more single base-pair mismatches, additions, and/or deletions, but is still capable of forming a complex with the binding substrate under the selected hybridization, binding or association conditions. In one embodiment, complementary sequences may hybridize through Watson-Crick base pairing (A-T or A-U and C-G or alternatively pairing with inosine). In a further embodiment, complementary sequences may hybridize through Hoogstein base pairing. In alternative embodiment, complementary sequences may form a catalytic complex, such as PNA-DNA-dye catalytic complex. In other words, the dye may accelerate or promote catalytic complex formation between the nucleic acid analog and the binding substrate.

The terms "complex," "catalytic complex," "dye catalytic complex" or "nucleic acid analog/binding substrate/dye complex" are used interchangeably throughout the specification and generally refer to an association between a dye, nucleic acid analog and a nucleic acid analog binding substrate (polynucleotide, DNA, RNA, etc.) in a manner that forms a catalytic complex and permits detecting the presence of singlet oxygen or other reaction products. Without being bound by a particular theory, formation of a duplex, triplex, Watson-Crick base pairing, Hoogstein base pairing, or any other yet undefined binding or association is contemplated herein. As such, the term "complex" is not limited to any particular physical or structural relationship between the elements of the complex.

The term "reaction product(s)" encompasses primary and secondary reaction products, as defined below, produced directly or indirectly by the catalytic complex when exposed to light.

Any of the products of the reaction of the dye with the nucleic acid analog/analyte complex may be detected by methods that are independent of the direct measurement of the loss of color due to breakdown of the dye.

The term "primary reaction product(s)" refers to any products of the reaction between the nucleic acid analog/binding substrate/dye complex and light. Some exemplary reaction products include, e.g., the singlet oxygen, and the following molecules:

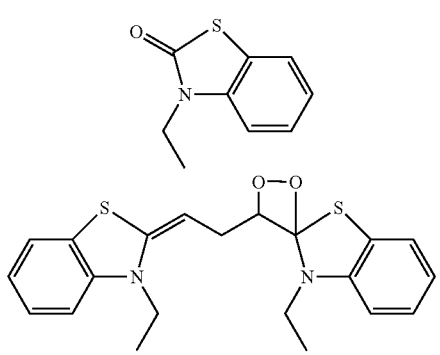

and/or

Other reaction products are also included.

For example, the presence, absence or amount of singlet oxygen can be measured directly by methods including but not limited to measurement of the singlet oxygen infrared emission at about 1270 nm (Khan and Kasha, 1979), the fluorescence of the singlet oxygen dimol at about 634 nm (Mulliken, 1928), electron spin resonance, calorimetry, photo ionization, mass spectroscopy. The amount of singlet oxygen could be determined by measuring the amount of singlet oxygen decay by methods such as time dependent thermal lensing (Rossbroich et al., 1985).

The term "secondary reaction product(s)" refers to any detectable products of the reaction between the singlet oxygen and another chemical entity, such as DPAX, DMAX, ATTA-$Eu^{3+}$ and 4,4'(5 ')-bis[2-(9-anthryloxy)ethylthio] tetrathiafulvalene, except cyanine dyes). For example, the reaction of singlet oxygen with cholesterol leads to a stable product, 3β-hydroxy-5α-hydroperoxt-$D_6$-cholestene. The amount of singlet oxygen could be determined by measuring the interaction of singlet oxygen with triplet β-carotene (Farmilo and Wilkinson, 1973). The presence of single oxygen can be determined by various methods including, but not limited to, measuring the generation of stable nitroxide radicals from sterically hindered amines (Lion et al., 1976), alteration of scavengers, altered reactions in the presence of $D_2O$, increased fluorescence of a singlet oxygen sensor molecule, such as sensor green (Invitrogen), or sensors for detecting singlet oxygen and superoxide production such as DanePy and HO-2941 (Barta et al., 2002).

The term "singlet oxygen sensor molecule" refers to a chemical compound (e.g., singlet oxygen sensitive dye) that is capable of interacting with the singlet oxygen, and/or any other molecule(s) that react with the singlet oxygen, in a detectable manner (except cyanine dye), such as DPAX, DMAX, ATTA-$Eu^{3+}$ and 4,4'(5')-bis[2-(9-anthryloxy)ethylthio]tetrathiafulvalene.

The term "rate" refers to a change in a property of a composition or compound relative to a particular period of time. A rate may be described in terms of a specific rate constant. A rate may be determined by making measurements over a period of time. A rate may be described by making measurements, determined by measurements at two different time points in a process or by making measurements at least three, at least four, or at least five time points. A rate may also be determined based on a single measurement and a known quantity, such as a previously known or calculated quantity. A rate may be expressed in quantitative or qualitative terms (e.g., a change is "fast" or "slow"). A rate may be determined by comparing a property or compound to a reference value, or by observation of changes in a given property or compound over time, using standard methods.

As used herein, the term "relative rate" refers to the rate of one process compared to the rate of another process or of the same process in another reaction. A "relative rate" may be approximate (e.g., the rate of one process may be "faster" or "slower" than the rate of another process) or quantitative (e.g., comparing measured rate constants of two processes).

As used herein, the term "dye" refers to a compound that can generate a reaction product, such as singlet oxygen, in the presence of the nucleic acid analog, the binding substrate, and light.

The dye may exhibit the property under certain conditions, such as binding or forming a catalytic complex or otherwise being in contact with a nucleic acid analog/binding substrate. The term "light reactive dye" means a dye that reacts to light exposure, such that when the light reactive dye is associated in a complex with complementary binding molecules, at least one of which is a nucleic acid analog, such as a PNA molecule, the light reactive dye confers a property on the complex that, in response to exposure of the complex to light, results in the catalytic production of singlet oxygen and/or other reaction products. In some embodiments, the complementary polynucleotides of the complex may comprise nucleic acid analog and a standard nucleic acid. In other embodiments, the complex may comprise two nucleic acid analogs. For example, complexes formed between the light reactive dye and complementary polynucleotides comprising at least one nucleic acid analog polynucleotide are referred to herein as "light reactive complexes," or "PNA/DNA/dye complexes," or "nucleic acid analog/binding substrate/dye complexes," or "nucleic acid analogs/dye complexes."

The term "mixture" includes a mixture of components, including where one or more of the components of the mixture are bound to a solid substrate, or where one or more components of the mixture are in a liquid solution.

The term "sample" refers to a liquid sample of any type (e.g., blood, serum, water, urine, fecal matter, sputum, or lysate or extract of a solid sample), a solid sample of any type (e.g., fecal matter, cells, food, ice, dirt, grain, or material acquired from a surface), an airborne sample of any type, and/or a material embedded in a gel material and/or any solid-phase material, such as agarose, acrylamide, or gelatin. The methods of the invention may also utilize solid or semisolid supports to immobilize one or more molecules that specifically bind to and capture an analyte of interest, so that components of the sample that do not bind to the solid support can be washed from the solid support, leaving only the analyte of interest, if present in the sample. Most often, the nucleic acid analog or analyte is immobilized. There are many types of solid supports that the nucleic acid analog or analyte molecules may be attached to, including but not limited to: cast membranes (nitrocellulose, nylon), ceramic, track-etched membranes (TEM), polyvinylidenedifloride, latex, paramagnetic beads, plastic supports of all types, gels, glass, powdered silica or alumina on a support matrix. If a grid pattern is used, the nucleic acid analog molecule/solid support forms a microarray. In another variation, the nucleic acid analog or analyte molecules may be covalently modified to include a linking moiety, such as a biotin or amide linkage, which binds to membranes. In a further variation, the nucleic acid analog or analyte molecules may be immobilized via sequence specific hybridization to one or more sequences.

Any means of attaching a nucleic acid analog or other components of the complex to a support is contemplated. In one aspect, the nucleic acid analog may be attached directly to a membrane. The nucleic acid analog may be a PNA (e.g., A Giger et al., NUCLEOTIDES AND NUCLEOSIDES 17:1717-1724 (1998)). A solution of nucleic acid analog molecules (in water) is simply applied to a charged or chemically modified filter and allied to air dry. The filter is then used for hybridization.

In another aspect, a biotin labeled nucleic acid analog molecule may be attached to a streptavidin-coated surface, such as a bead or well (see, e.g., Chandler et al., ANAL. BIOCHEM. 283:241-249 (2000)). Biotin labeled nucleic acid analog molecules mixed with streptavidin-labeled latex or polycarbonate beads. The biotin binds strongly with streptavidin, allowing the nucleic acid analog molecule to bind to the bead in a unidirectional fashion. The beads are then applied to a non-charged membrane with a mesh size 25-30% greater that the diameter of the bead. Beads become trapped in the mesh, hence making a localized area of "attached nucleic acid analog molecules." Direct synthesis of nucleic acid analog molecules on a solid support such as a polypropylene membrane may be accomplished using standard 9-fluorenylmethoxycarboyl (Fmoc) protein synthesis chemistry (see, e.g., S. Matysiak et al., BIOTECHNIQUES 31:896-904 (2001)) or tBoc protein synthesis chemistry (Nielsen, 1991, supra).

In another aspect, the nucleic acid analog molecules may be fixed to a glass or other solid support by applying a solution containing nucleic acid analog molecules in water directly to the glass or other support and letting it air dry.

Other methods of immobilization are also contemplated.

Any analyte, or group of analytes, may be detected by the solid support based system. For example, a solid support can contain multiple nucleic acid analog molecules immobilized on a solid support. A control nucleic acid analog that does not form a nucleic acid analog/analyte/dye complex, may be included on the solid support.

The solid support-based assay system may be used to detect at least one analyte. In other variations, the solid support-based system detects or measures the presence or absence or amount of at least about 8, at least about 10, at least about 20, at least about 30, at least about 40, at least about 50, or at least about 60 different analytes. In another variation, the solid support-based system detects and distinguishes amounts of 60 or more analytes.

As used herein, the terms "array" or "microarray" refer to a set of analytes immobilized onto one or more substrates so that each analyte is at a known location. Alternatively, the set of analytes may be in solution, respectively in different receptacles of a microtiter dish, and therefore, located at known locations. In one embodiment, a set of analytes is immobilized onto a surface in a spatially addressable manner so that each individual analyte is located at different and identifiable location on the substrate.

The term "chemical handle" refers to a component that may be attached to a complex as described herein so as to facilitate the isolation, immobilization, identification, detection and/or increased solubility of the complex. Suitable chemical handles include, for example, a polypeptide, a polynucleotide, a carbohydrate, a polymer, or a chemical moiety, and combinations or variants thereof.

The term "observing" means detecting a change in a property or value, either directly or indirectly, by means of visual observation, instrumentation, or receipt of data.

The term "reporter molecule," as used herein, means a catalytic complex (i.e., the nucleic acid analog/nucleic acid analog binding substrate/dye complex) when used to report the presence, absence and/or amount of another analyte. In one embodiment, an analyte specific binding compound is bound directly or indirectly to the nucleic acid analog and/or to the nucleic acid analog binding substrate of the reporter molecule. The analyte specific binding compound binds to the analyte, if present in the sample. The catalytic complex binds to the analyte via the analyte specific binding compound. Specifically, the catalytic complex of the present invention may be used to generate a detectable signal that is indicative of the presence of the analyte, such as a macromolecule (i.e., a protein) or a nucleic acid. For example, the nucleic acid analog specific binding substrate may be a nucleic acid molecule bound to an antibody that specifically binds to a macromolecule analyte. In another example, the nucleic acid analog may be bound to an antibody that specifically binds to a protein analyte. In yet another example, either a nucleic acid molecule or a nucleic acid analog may be bound to a macromolecule that specifically binds to an antibody analyte. An "analyte-specific reporter complex" refers to a reporter complex that specifically binds to the analyte of interest. The analyte-specific reporter complex can be captured by, for example, binding the antibody to an antigen immobilized (i.e., bound, trapped, captured, attached, etc.) on a solid support. Analyte-specific reporter complex that does not bind to the solid support is removed by washing the solid support.

Dyes

Dyes suitable for use in the methods and complexes of this invention include, for example cyanine dyes, thiacyanine dyes and/or carbocyanine dyes. Some specific examples of dyes include 3,3'-diethylthiacarbocyanine iodide, 3,3'-dimethylthiacarbocyanine iodide, 3,3'-dipropylthiacarbocyanine iodide, 1-1'-Diethyl-2,2'-carbocyanine iodide, 3,3'-Diallylthiacarbocyanine Bromide, 3,3'-Dipentylthiacarbocyanine iodide, 3,3'-dibutylthiacarbocyanine iodide, 2-((1E,3Z)-3-(3-Ethylbenzo[d]thiazol-2(3H)-ylidene)prop-1-enyl)-3-methylbenzo[d][1,3]selenazol-3-ium iodide (OR by another name 3-ethyl-3'-methylselenocarbocyanine iodide), and 3-Ethyl-2-((1E,3Z)-3-(3-ethylbenzo[d][1,3]selenazol-2(3H)-ylidene) prop-1-enyl)benzo[d][1,3]selenazol-3-ium hydrogensulfate (OR by another name 3,3'-diethylselenocarbocyanine hydrogensulfate).

Suitable dyes can be identified using any of a variety of screening methods. The dyes of the present invention promote and accelerate the formation of a catalytic complex, which results in the production of singlet oxygen and/or other reaction products that can be detected and correlated to the presence or absence, or amount, of an analyte present in a sample. For example, in preferred embodiments, the catalytic complex produces singlet oxygen, which can then be detected qualitatively to determine the presence or absence of the analyte, or may be detected quantitatively to determine the amount of analyte present in the sample. By way of example, a nucleic acid analog/nucleic acid analyte can be used to identify suitable dyes by comparing the relative production of singlet oxygen of the various dyes in complex with the nucleic acid analog/nucleic acid analyte and light. Preferably, the combination includes other components and is maintained in conditions to promote formation of a complex of the dye and the nucleic acid analog/nucleic acid analyte, using such components and conditions that are well known in the art. Suitable conditions and components are described herein. The candidate dye is then preferably added; more preferably, the candidate dye is added to separate aliquots of the combination, such that the dye is present in the separate aliquots at varying concentrations. Yet more preferably a buffer is added. The order of addition is not critical; the components can be added in any order. Once the reaction mixture is formed, a light stimulus is applied. The amount or rate of production of the reaction products over time is then determined directly or indirectly, and is correlated to the presence or absence, or amount, of a reaction product in the sample. The amount or rate of production may be compared to a reference value characteristic of the amount or rate of production of the reaction products of the reaction mixture in the absence of the complex. In other embodiments, the amount or rate of production of the reaction products in the presence of a first analyte is compared to the amount or rate of production of the reaction products in the presence of a second analyte, wherein the particular amount or rate of production can be correlated to the particular analyte present in the sample.

In certain embodiments, the reference value is characteristic of the absence of the analyte or the presence of the analyte, which can be single-stranded or double-stranded nucleic acid or any other target molecule. In other embodiments, the reference value is characteristic of a non-zero concentration of the analyte. Preferably, the reference values employed include those characteristic of a zero and at least one non-zero concentration of the analyte, respectively.

In certain embodiments, the amount or rate of production of the primary reaction products from the formation of the catalytic complex is correlated to the ability of the dye to accelerate and promote production of the reaction products, and used to identify dyes having greater utility in the present invention. Dyes that accelerate or promote production of reaction products in the reaction mixture are particularly preferred, where the mixture exhibits a different amount or type of reaction product produced over time (a rate) or at a single time, compared to a reference value. The relative rate (or amount) of production of reaction products of the mixture is correlated with the presence or absence or amount of the analyte in the sample. Dyes that contribute to the generation of singlet oxygen or other reaction products, where the reaction mixture produces singlet oxygen in the presence of a nucleic acid analog/binding substrate complex and light, are preferably selected.

Analytes

The analyte may include any target molecule that is being detected or measured either directly or indirectly by the methods and complexes described herein. The analyte may be any polynucleotide analyte, including naturally occurring, synthetic, and amplified polynucleotides. Other types of analytes may be single-stranded, double-stranded, triple-stranded, or yet greater degree multi-stranded. Non-limiting examples of analytes include DNA, RNA, regulatory RNA, mRNA, regulatory microRNA, siRNA, artificial RNA, chimeric RNA, non-coding RNA and armored RNA. Other non-limiting examples of analytes include epigenomic DNA, epigenetic DNA, in vitro amplified DNA, and chimeric DNA. The analytes may contain single nucleotide polymorphisms (SNPs), insertions or deletions, copy number variations or other differences that are identified or quantitated by the methods disclosed herein. Analytes may also include: other biological molecules (such as proteins, antibodies, carbohydrates, proteoglycans, lipids, or hormones), pharmaceuticals or other therapeutic agents and their metabolites, drugs of abuse (for example amphetamines, opiates, benzodiazepines, barbiturates, cannabinoids, cocaine, LSD and their metabolites), explosives (for example nitro-glycerine and nitrotoluenes including TNT, RDX, PETN and HMX), and environmental pollutants (for example herbicides, pesticides). The analyte can also be a nucleic acid analog.

Light Stimulus

Light stimulus can be provided to a sample that may or may not contain an analyte, nucleic acid analog, and dye mixture either concurrently with the production of the mixture or at a specified time after the production of the mixture. The light stimulus may be in the visible spectrum or outside the visible spectrum. The light stimulus may be white light of a number of wavelengths. Alternatively, the light stimulus may be a specific wavelength or wavelengths, or range of wavelengths. The light stimulus may be a filtered light. The light stimulus may comprise a specific range of wavelengths. The range of wavelengths may be from a blue light stimulus, a green light stimulus or any other desirable light stimulus.

The light stimulus may be applied to the mixture for a specified amount of time, such as from about 1 second to about 20 minutes. Any length of time in between the specified range from about 1 second to 20 minutes is also contemplated. For example, the light stimulus may be applied to the mixture for about 30 seconds or 1 minute. The light stimulus may be applied to the mixture as bursts of light or as a continual light.

Light sources are known in the art. Different light sources result in different reaction rates because of differences in intensity or wavelength of the light sources. Examples of light sources include Xenon arc lamp (Ushio, #UXL-451-O), Sylvania dulux S9W CF9DS/blue and Sylvania Cool White T8-CW (OSRAM SYLVANIA, Danvers, Mass.), General Electric T8-C50 GE Lighting, Cleveland, Ohio), Osram F9TT/50K (OSRAM GmbH, Munich, Germany), and Fritz Aurora 50/50 (Fritz Industries, Inc., Mesquite, Tex.). Other light sources include light emitting diodes (LEDs) that produce a specific range of wavelengths, such as Jameco #183222 a 470 nm LED, Jameco #334473 a 505 nm LED, Jameco #183214 a 515 nm LED, or a white multiwavelength (420-700 nm) LED #LLW5210200. LEDs emit light at least one peak wavelength, and in certain embodiments can emit light at multiple peaks. In certain variations, the bandwidth of the LED can be as small as 1 nm, or as large as 20 nm. Other light sources include commercially available halogen light sources, such as halogen headlamps (NAPA Auto Parts, Atlanta, Ga.).

The light stimulus may also have a specific intensity. In certain variations, a 15-Watt light source at 555 nm produces between about 400 foot-candles and 2000 foot-candles of illumination. In other variations, the light stimulus is one or more LEDs, preferably it is a bank of LEDs, the power of which varies from 500 µW to 4000 µW/cm$^2$ at 3.5 inches away from the light.

Those of skill in the art will recognize that the optimal light stimulus may be determined without undue experimentation for a specific dye, or a specific nucleic acid analog, binding substrate, and dye complex in the mixture. A single set of temperature and concentration conditions can be optimized for a specific mixture.

Dye-PNA-DNA Complex as a Catalyst

Previous literature describes the interaction of cyanine dyes with PNA or DNA or PNA-DNA duplexes[32, 35, 38, 40-41]. Cyanine dyes are known to form dimer or higher aggregates in the minor groove of these duplexes and result in spectroscopic changes. In the present study, the UV-vis spectra (FIG. 1A) of various dyes in the presence of PNA-DNA duplexes demonstrate the formation of a dye-PNA-DNA complex with DiSC$_2$(3), DiSC$_3$(3), DiSC$_4$(3), and DiSC$_5$(3), but not with DiSC$_{py}$(3). Fluorescent quenching of DiSC$_2$(3) in the presence of PNA-DNA duplexes demonstrates the cooperative nature of the binding interaction of this dye with the minor groove of the duplex. CD spectra also show that DiSC$_2$(3) interacts with PNA-DNA in an aggregate manner.

In the presence of a PNA-DNA duplex, a novel DiSC$_2$(3)-PNA-DNA complex can form. This complex is capable of rapidly catalyzing the accelerated photobleaching of a large excess of DiSC$_2$(3), possibly through a singlet oxygen mediated mechanism (for cyanine dyes as $^1O_2$ sensitizers, see ref. 42). In a typical 50 µl smartDNA assay with DNA equivalent to 400,000 *M. tuberculosis* genomes causes the complete photobleaching of a large amount of dye, approximately 10$^{14}$ molecules, in 4 minutes when the reaction mixture is exposed to 470 nm light. The calculated turnover rate of the dye molecules per PNA binding site on the target molecule at varying DNA target amounts remains surprisingly constant. Approximately 33,000 dye molecules are turned over per second. This suggests that the dye-PNA-DNA complex is acting in a catalytic manner to turnover the excess dye in the reaction. This fast turnover rate is not without precedent. The enzyme acetylcholinesterase turns over 25,000 molecules per second and carbonic anhydrase turns over 600,000 molecules per second (FIG. 5).

In the smartDNA system, the structure of the cyanine dye that can (1) form a useful catalytic complex with PNA-DNA duplexes, and (2) produce singlet oxygen, and (3) is sensitive to photobleaching in the presence of singlet oxygen has low tolerance for changes. In addition to DiSC$_2$(3), DiSC$_3$(3), DiSC$_4$(3), DiSC$_5$(3) and DiSC$_{py}$(3), cyanine dyes with other modifications at the chromophore were screened under a restricted set of conditions. Oxazole substitution for the thiazole, or an increase in the length of the methane bridge between the 2 heterocycles, such as $DiSC_2(5)$ did not show accelerated photobleaching in the PNA-DNA oligomer duplex system. There is no observable difference between the photobleaching rate of the free dye in the presence or absence of a PNA-DNA oligomer duplex. Thus, we concluded in these studies that the benzothiazole heterocycle and the length of the bridge are all critical for the specific interactions that result in accelerated photobleaching in genomic system. However, it is not known at which of the three steps the limitation occurs or if this limitation can be overcome under different reaction conditions.

With $DiSC_2(3)$, exposure of dye-PNA-DNA complex (pre-annealed PNA-DNA oligomer duplex) to LED light sources near the dye's absorption maxima or longer wavelengths, (574 and 640 nm), or shorter wavelengths (390 and 410 nm) accelerated photobleaching was not observed. Exposure of dye-PNA-DNA oligomer complexes to 470, 490, or 515 nm LED light sources did cause accelerated photobleaching. The 470 nm wavelength proved optimal. Compared to 490 and 515 nm, exposure to 470 nm light had a faster accelerated photobleaching rate and a slower rate of photobleaching of the free dye (data not shown). We suggest that the generation of singlet oxygen requires a stable excited triplet state, and dyes that form H aggregates which absorb at 470 nm were more effective than monomeric dyes in forming the required stable triplet state. The H-aggregate formed should have a longer singlet lifetime, due to the forbidden radioactive transition to the ground state, thus is more efficient for the energy transfer of intersystem crossing than other configurations that resulted in absorbance at different wavelengths[43].

Substituent Effects on Catalyst Formation

Even for dye derivatives with the same thiacarbocyanine chromophore, substituents at the N atom play a significant role in the interaction of the dye with pre-annealed PNA-DNA duplex and/or on the rate of the accelerated photobleaching of the dye in the genomic DNA system. Detailed studies were performed with $DiSC_2(3)$, $DiSC_3(3)$, $DiSC_4(3)$, $DiSC_5(3)$ and $DiSC_{py}(3)$, which have substituents that increase the bulkiness at the N atom of the benzothiazole (shown in FIG. 4). The spectra of $DiSC_{py}(3)$ (3-alkylpyridinium substituents) with the PNA-DNA oligomer duplex showed no aggregate band at 470 nm. Thus, there is no or very low interaction affinity between $DiSC_{py}(3)$ and the PNA-DNA oligomer duplexes. For $DiSC_5(3)$, the dye with the longest side chain in this group, the aggregate band at 470 nm is present but at low amounts and the 556 nm monomer band is present at high amounts. This result suggests a decreased interaction affinity of $DiSC_5(3)$ for the PNA-DNA duplex. $DiSC_4(3)$ does exhibit the 470 nm aggregate band and moderate amounts of the 556 nm monomer band. The decrease in the 556 nm band is directly related to the rate of the accelerated photobleaching in a smartDNA reaction with dye-PNA-DNA oligomer duplex. In these reaction conditions, photobleaching experiments with $M.\ tuberculosis$ genomic DNA and dyes other than $DiSC_2(3)$ did not exhibit the same accelerated photobleaching reaction. Although as indicated in FIG. 4 there is a modest level of accelerated photobleaching with these other dyes. Among other things, these results suggest that the substituents on the nitrogen atom of the benzothiazole rings are important for the formation of a PNA-DNA-dye complex and are especially important for the formation of the complex that causes the accelerated photobleaching of the dye in the presence of genomic DNA and/or for the susceptibility of the 'un-PNA-DNA-complexed'-dye to singlet oxygen oxidation.

The efficiency of $^1O_2$ generation is dependent on the energy level of the excited triplet state of the photosensitizer, in this case, proposed to be the dye-PNA-DNA complex. Different substituents result in different alignment of the dye molecules in the complex; this results in different excited triplet state energy levels and the very different reactivities that are observed. Additional studies to investigate the effects of the substituents on the energy level of the dye-PNA-DNA complex formed are planned. Also, changes in substituents change the susceptibility of the dye molecule to photobleaching. We have observed that $DiSC_{py}(3)$ alone in buffer has the slowest background photobleaching rate. Similarly, $DiSC_3(3)$, $DiSC_4(3)$ and $DiSC_5(3)$ all have slower background photobleaching rates than $DiSC_2(3)$.

Thus, $DiSC_3(3)$, $DiSC_4(3)$ and $DiSC_5(3)$, appear to bind to the PNA-DNA oligomer duplex as aggregates. However, under the conditions we tested, there is minimal accelerated photobleaching reaction with these dyes in the presence of PNA probe and $M.\ tuberculosis$ genomic DNA. This might be due to several factors, including (1) the interaction affinity of dye to PNA-genomic DNA, (2) the structure of the dye-PNA-DNA complex and its efficiency at singlet oxygen generation, (3) the energy level of the excited states of dye molecules in the complex, and/or (4) the susceptibility of the dye to oxidation.

Rapid Dye Mediated PNA-DNA Binding

PNA invasion of duplex DNA, which requires breaking the Watson-Crick Hydrogen bonding of duplex DNA, is a very slow and unfavorable process[44]. Conjugation of acridine to a PNA[45], or bis-PNA in the presence of quinoxaline antibiotics[46] has been reported to improve duplex DNA invasion. However, in the smartDNA system with PNA probes that have been empirically selected, a sequence specific PNA-genomic DNA complex is formed at room temperature in less than 10 minutes. DNA from other organisms has been tested with TB14, the $M.\ tuberculosis$ specific PNA probe, and show near background accelerated photobleaching (FIG. 3). Whether this complex is formed solely through a modified Watson-Crick hybridization process involving the presence of the cyanine dye or some completely different mechanism of interaction is under active investigation.

Singlet Oxygen Generation

Figure 2:
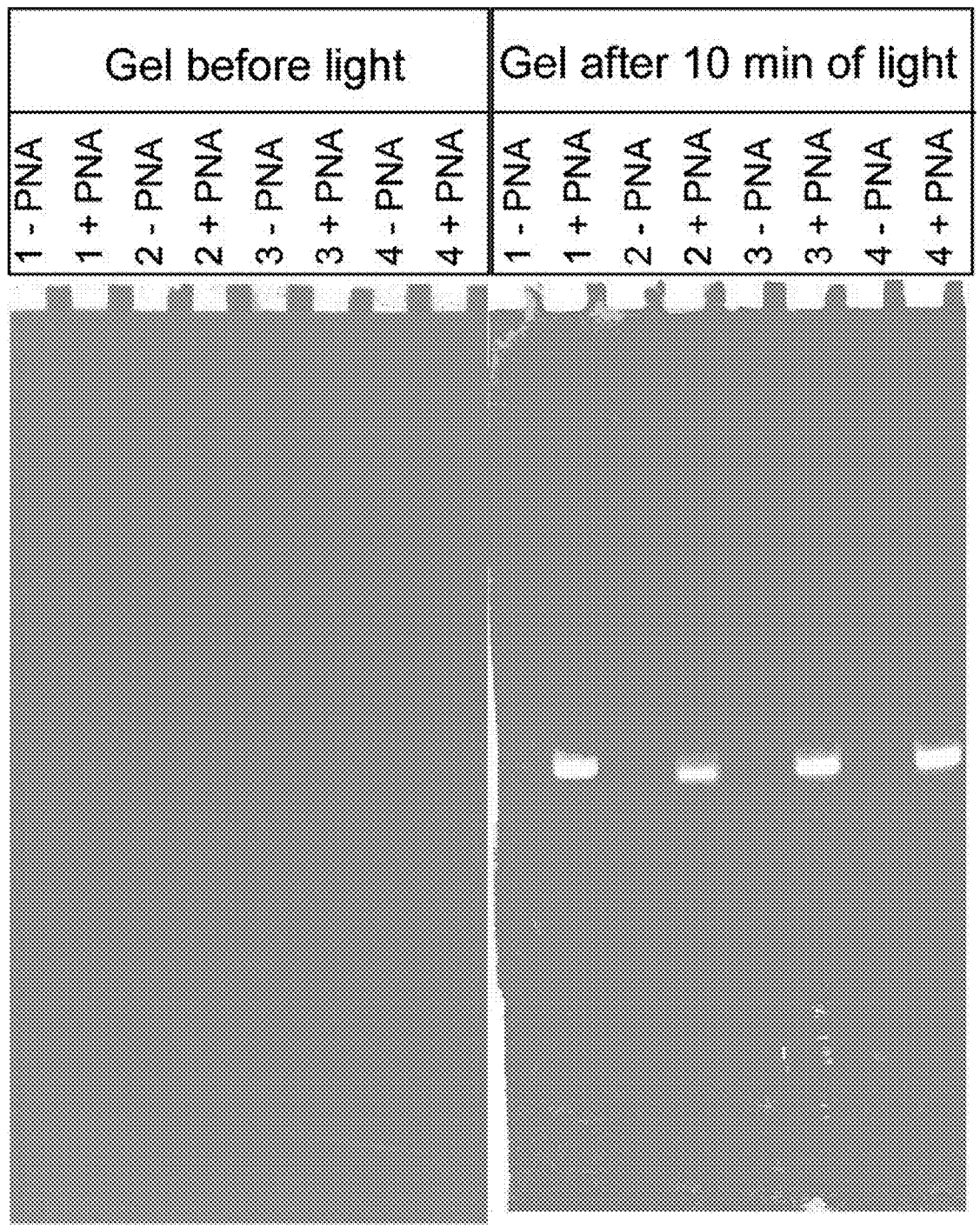
FIG. 2 is a picture of a smartDNA assay run in a gel. Equal amounts of PNA and DNA complementary oligonucleotide were pre-annealed. 2 pmoles of DNA oligonucleotide or of the pre-annealed PNA:DNA duplex (2 pmoles each) were loaded onto a 1×TBE, 10% (19:1) non-denaturing polyacrylamide gel. After electrophoresis, the gel was stained for 30 minutes in a 1×TBE solution containing 15 μM $DiSC_2(3)$ dye. The gel was illuminated with a standard UV light box and black and white gel photos were taken at time zero and after 10 minutes exposure of the gel to a 15W white fluorescent light (Aurora 50/50, Fritz Industries, Mesquite, Tex.) at irradiance of 2 mW $cm^2$. The bands with accelerated photobleaching (absence of pink color in reality and absence of black in this figure) correspond with PNA-DNA duplexes. The sequences used are indicated in the Table 1 below.

Without being bound by a specific mechanism, FIG. 5 shows the proposed mechanism for the overall process of the singlet oxygen generation and resulting accelerated photobleaching of dye. The presented spectral evidence suggests that a complex containing an H-aggregate of the dye forms when complementary PNA and DNA sequences bind to each other. PNA-DNA hybrids run out into a gel and stained with the dye exhibit photobleaching only where the hybrid migrates (FIG. 2). This is consistent with the notion that the dye-PNA-DNA complex is required for photobleaching. Removing oxygen from a reaction solution of the dye slows its photobleaching. Azide also quenches the photobleaching reaction; apparently catalyzed by the complex. The structure of the characterized product produced from photobleaching free dye in solution is consistent with the involvement of singlet oxygen photo oxidation of the bulk dye present in solution. Moreover, during this proposed $^1O_2$ mediated process, the DNA might undergo oxidation; partially supported by the observation that re-addition of PNA and dye after the photobleaching reaction did not resume the reaction. In this case, the oxidized DNA is the reaction product and may also be detected. The presence of oxidized nucleic acids may be detected through methods, such as high-performance liquid chromatography coupled to electrochemical detection (HPLC-EC) for the detection of 8-oxo-7,8-dihydro-2'-deoxyguanosine (8-OxodGuo)[55], 5-hydroxy-2'-deoxycytidine (5-OHdCyd), 5-hydroxy-2'-deoxyuridine[56] and 8-oxo-7,8-dihydro-2'-deoxyadenosine (8-OxodAdo)[57], and gas chromatography coupled to electron impact mass spectrometry (GC-EIMS)[58].

The simplest mechanism is that the $DiSC_2(3)$-PNA-DNA complex generates singlet oxygen when exposed to 470 nm light. Once formed, the singlet oxygen is free to diffuse into solution and causes the oxidation of the great excess (>99%) of free dye that is in solution and likely dye that is associated with DNA. Thus, the reaction rate should be directly dependent on the concentration of the dye-PNA-DNA catalyst present. Because the DNA target is the limiting reagent and all other reactants are present in about $10^5$- to $10^6$-fold excess, the predicted rate of photobleaching should be proportional to the DNA target concentration. This can be observed experimentally.

Utility of smartDNA

The sequence specific accelerated photobleaching reaction of $DiSC_2(3)$ in the presence of the PNA probe and genomic DNA target forms the very interesting photochemical basis for a sensitive, rapid, simple, and potentially inexpensive method for DNA detection. The accelerated photobleaching is induced with an inexpensive LED and detected with a simple photodiode circuit. Measurement of the dye photobleaching rate in solution enables sensitive inexpensive DNA determinations to be performed. The method takes advantage of PNA's natural high affinity and specificity for DNA. This is further improved by the discovery of a rapid room temperature binding process that occurs in the presence of the dye.

When combined with suitable sample processing and activating-reading hardware, the smartDNA technology could be used to produce sensitive, rapid and potentially inexpensive diagnostic assays. Due to its inherent simplicity, the smartDNA detection is ideally suited for rapid diagnostics of infectious disease in resource constrained or point of care settings. To that end, assay development work is proceeding on applying the method to the detection of *M. tuberculosis*.

Applications

The methods of the present invention may be practiced in various applications. As noted above, the methods may be practiced, for example, to identify and analyze analytes present in a sample in solution. The methods may alternatively be practiced to identify multiple analytes of interest that are immobilized on a solid or semi-solid substrate. In yet other embodiments, the methods may be practiced by immobilizing the nucleic acid analog to a solid substrate, or by immobilizing all or part of the reporter complex to a solid substrate. Such variations are well known to those skilled in the art and can be selected and designed according to the needs of the particular application.

EXAMPLES

Materials

The cyanine dyes with counterions 3,3'-diethylthiacarbocyanine ($DiSC_2(3)$), 3,3'-dipropylthiacarbocyanine ($DiSC_3(3)$), 3,3'-dibutylthiacarbocyanine ($DiSC_4(3)$) and 3,3'-dipentylthiacarbocyanine ($DiSC_5(3)$) were purchased from Sigma-Aldrich (St. Louis, Mo.) or FEW Chemicals (Wolfen, Germany) and were used without further purification. 3,3'-Di(3-propylpyridinium)thiacarbocyanine ($DiSC_{py}(3)$) was synthesized in the laboratory of Dr. Jerzy Paczkowski. Stock solutions of 7.5 mM dye in DMSO were prepared and stored at −20° C.

PNA oligomers (Table 1) were purchased from Panagene (Korea, www.panagene.com), and re-suspended in molecular biology grade water (HyClone, Logan, UT) and stored at −20° C. To increase solubility all PNA oligomers have a N-terminal lysine. PNA oligomers with a C-terminal lysine had characteristics similar to the PNA oligomers with a N-terminal tag. DNA oligomers (Integrated DNA Technologies, Coralville, IA) were re-suspended in molecular biology grade water and stored at −20° C. Buffers were purchased from Research Organics (Cleveland, OH). Homopipes powder was dissolved in microbiology grade water to 20 mM, adjusted to pH 5.0 with 5N NaOH, and filtered through 0.2 μgm sterile filter (Nalgene PES filter, part number 566-0020, Nalge Nunc International, Rochester, NY). EDTA was purchased as 500 mM solution (Teknova, Hollister, CA), and diluted to the required concentration. Genomic DNA of Mycobacterium tuberculosis (MTB) strain CDC1551 was obtained from Colorado State University. Genomic DNAs from other bacteria were purchased from ATCC (Manassas, VA) (*Escherichia coli* (700928D), *Staphylococcus aureus* (108320D), *Streptococcus pneumoniae* (BAA-334D), *Haemophilus influenzae* (51907D), *Neisseria meningitidis* (BAA-335D), *Pseudomonas aeruginosa* (47085) and *Klebsiella pneumoniae* (707721D). Human placental DNAs (lots 14686, 02153787, and 123K3786) were purchased from Sigma-Aldrich (St. Louis, MO). All DNAs were re-suspended in molecular biology grade water and stored at −20° C.

Equipment

Reaction mixtures were prepared in 384-well white wall, optical bottom microplates (Nunc 242763, Nalge Nunc International, Rochester, N.Y.). Measurement of UV-vis, fluorescence spectra, and time-course assays of the decrease in absorbance at 556 nm with exposure to 470 nm light were performed with a Tecan Safire$^2$ microplate reader (Tecan US, Durham, N.C.). A solid state smartDNA activator was developed by Advanced Scientific Consulting (Toronto, Canada) and consists of 192 2000-mcd 470 nm light emitting diodes (LED), (Jameco Electronics P/N 183222, Belmont, Calif.) arranged in a 5×7 inch rectangular array placed 2 inches above the microplate surface. This configuration produced an irradiance of approximately 2 mWcm$^{-2}$ at the microplate surface. CD spectra were recorded on an Olis RSM 1000 circular dichroism spectrophotometer with a Quantum Northwest Peltier accessory located in the laboratory of Dr. Woolley at the Dept. of Chemistry, University of Toronto. Photolysis experiments were carried out in the laboratory of Dr. Jerzy Paczkowski.

Methods

For accelerated photobleaching assays performed in gels, the PNA-DNA oligomer duplexes were generated by mixing equal amounts of PNA (dissolved in water) and DNA complementary oligonucleotide (dissolved in 1×TE), heating the samples to 90° C. for 10 min and allowing them to cool slowly to room temperature in a heat block. 4 μL (2 pmoles) of DNA oligonucleotide or of the pre-annealed PNA:DNA duplex (2 pmoles each) was mixed with 4 μL of a 25% glycerol solution and loaded into a 1×TBE, 10% (19:1) non-denaturing polyacrylamide gel. After electrophoresis for 60 minutes at 300V, the gel was stained for 30 minutes in a 1×TBE solution containing 15 μM $DiSC_2(3)$. The gel was illuminated with a standard UV light box and black and white gel photos were taken at time zero and after 10 minutes exposure of the gel to a 15W white fluorescent light (Aurora 50/50, Fritz Industries, Mesquite, Tex.) at irradiance of 2 mWcm$^{-2}$. The photo shown (FIG. 2) has clear areas where the accelerated photobleaching occurred. The rest of the gel is black (and would be pink in color). For the accelerated photobleaching assays performed in microtiter plates, a series of dilutions of *M. tuberculosis* DNA were prepared and aliquoted to the wells of the microtiter plate. Dye with or without PNA was added to DNA samples with final concentrations of 9 µM dye, 160 nM PNA probe, in 10 mM homopipes buffer, pH 5.0 (0.05% Tween-80). The reaction mixtures were incubated at room temperature for 10 minutes in the dark. After an initial reading of the absorbance at 556 nm, the reactions were recorded by alternating exposure to light from the smartDNA activator for 2 minutes, and reading the absorbance at 556 nm, until the reactions were clear. Typically the absorbance change of $DiSC_2(3)$ in the reaction mixture was measured after the first 2 or 4 minutes of light exposure to determine the initial slope of the reaction (see Results for details).

For the spectra studies, 17mer PNA, 17mer single stranded DNA, or the 17 bp pre-annealed PNA-DNA duplex was titrated into a final dye solution of 9 µM, and final buffer of 10 mM Homopipes, pH5.0. Spectra were scanned immediately.

For the photolysis studies, 500 mg of $DiSC_2(3)$ was dissolved in 4 L of $KH_2PO_4/Na_2HPO_4$ buffer (pH 7.0) and placed in 5 L immersion well photoreactor equipped with 400 W medium pressure mercury lamp (Photochemical Reactors Ltd, UK). The solution, in the presence of oxygen (bubbled using the gas inlet tube), was exposed to the filtered mercury lamp emission for 10 to 12 hours until it became completely clear and the organic photobleached products were then extracted with chloroform. The UV portion of the mercury lamp's emission was eliminated using a liquid $K_2CO_3$ filter. The solvent was evaporated and the components of the residue were separated using column flash chromatography. This yielded two major products of which only one was stable. The structure of the stable product was analyzed using $^1H$ NMR spectroscopy.

Results

A previous report by Smith et al.[32] focused on the interaction of $DiSC_2(5)$ with PNA-DNA oligomer duplexes. However, they also briefly looked at the interaction of other cyanine dyes with the PNA-DNA duplex, including $DiSC_2(3)$. In these spectral studies they observed that there was a broadened absorbance band with $DiSC_2(3)$ upon interaction with the short PNA-DNA duplex. No further observations were reported. We were interested in further characterizing the interaction of $DiSC_2(3)$ with PNA-DNA duplex, and focused on the development of the unique interaction into a practical DNA diagnostics method.

I. Spectra Studies

The interaction of carbocyanine dyes with PNA-DNA duplexes were studied through UV-vis, CD and fluorescence spectra. Spectra were obtained for the dye only, the dye mixed with 17mer PNA, the dye mixed with the complementary 17mer DNA oligonucleotide, and dye mixed with a pre-annealed PNA-DNA 17mer duplex. For these experiments TB23, a 17mer PNA, with its complementary DNA strand was used. All spectra were obtained in the 10 mM, pH 5.0 Homopipes buffer.

1. UV-vis Spectroscopy

Figure 1A:
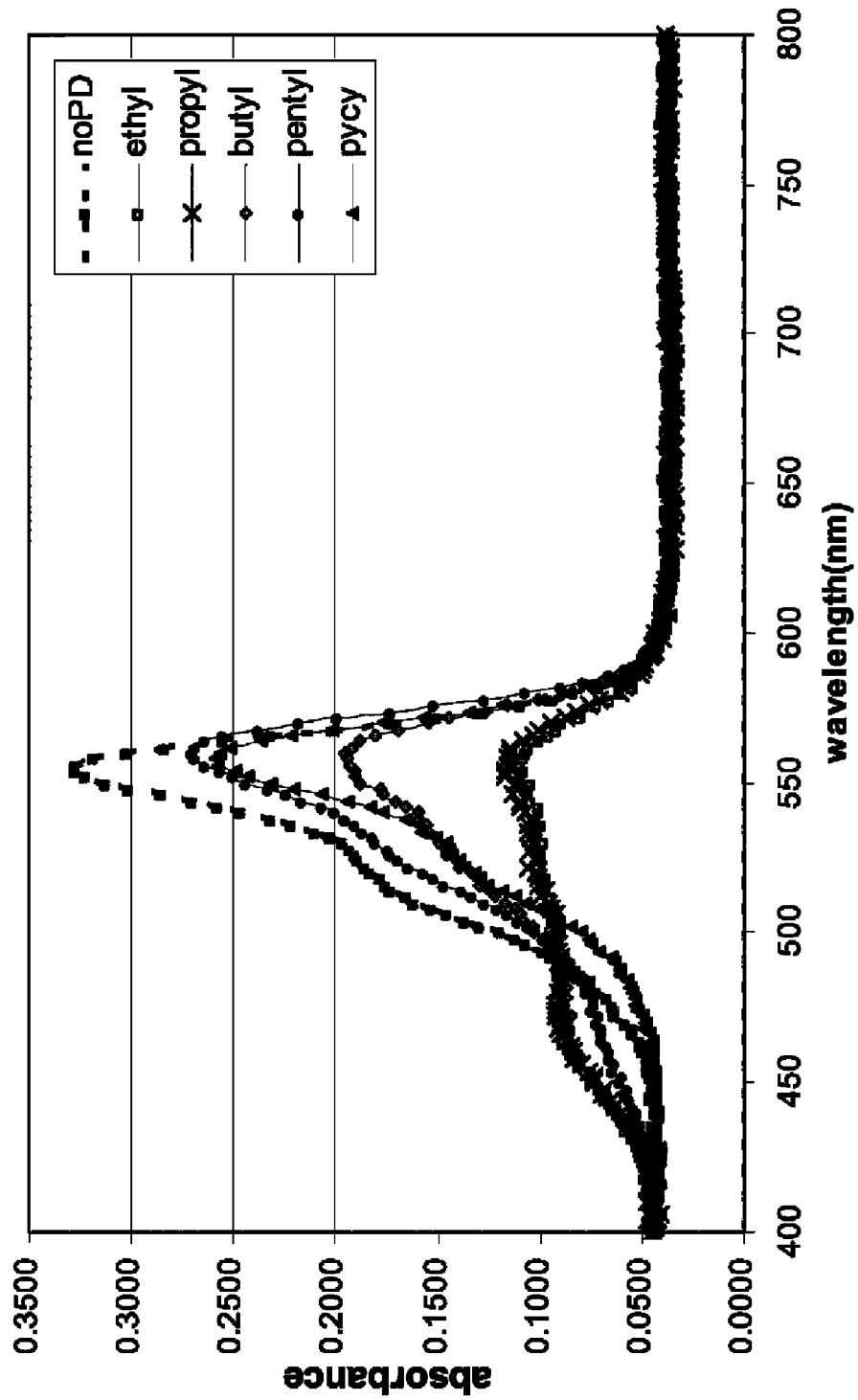
FIG. 1A is a graph of UV-vis spectra of N-3,3'-alkyl and tricationic dyes in the presence of 1 μM PNA-DNA (PD) oligomer duplex in pH 5 homopipes buffer, with dye final concentrations 9 μM. PNA used here is TB23, sequence shown in Table 1. $DiSC_2(3)$ alone in the same buffer is also depicted as no PD. The sequence of TB23 is GTTTTGGGTCTGACGAC (SEQ ID NO:1). All PNAs used have a C-terminal carboxamide and an N-terminal Lysine.

The UV-vis spectra of $DiSC_2(3)$ alone and of all 5 dyes (ethyl, propyl, butyl, pentyl and propylpyridinium) combined with a pre-formed PNA-DNA 17mer duplex are shown in FIG. 1A. All absorption spectra of dye alone in buffer are characterized by a major monomer absorbance band with maxima at 556 nm and a shoulder at 520 nm. The size of this shoulder decreases in a methanol solutions; thus, it may be due to the self aggregation of dye dimer in aqueous solutions[36,37]. Addition of PNA to solutions of any of the dyes did not result in a change in the spectra of the dye. Addition of single stranded oligomer DNA to solutions of the dyes resulted in a slight decrease in the monomer band. This indicates some interactions of the cationic dye with anionic DNA. However, the addition of PNA-DNA duplex to the dye solutions caused a dramatic decrease in the intensity of the monomer band and the appearance of a new band at approximately 470 nm, further blue shifted from the 556 nm maxima. The observed blue shift in the spectra is similar to that previously reported by Armitage and co-workers[32] upon the binding of $DiSC_2(5)$ to a 10 base pair PNA-DNA duplex. In this case, the formation of H-aggregate of $DiSC_2(5)$ with the PNA-DNA duplex, resulted in a blue-shifted band about 100 nm shorter than the monomer band.

$DiSC_{py}(3)$ did not show the new 470 nm band in the presence of the PNA-DNA duplex (FIG. 1A), although there was a slight shift in the monomer band, probably due to other mechanisms of interaction (such as weakly binding in the groove of the duplex, but failing to form an aggregate) between $DiSC_{py}(3)$ and the PNA-DNA duplex. However, the propyl, butyl and pentyl derivatives, ($DiSC_3(3)$, $DiSC_4(3)$, and $DiSC_5(3)$), all show the appearance of a 470 nm band upon addition of the PNA-DNA oligomer duplex (FIG. 1A). Bulkier substituents at 3, 3' positions, such as 3-propylpyridinium residues, might prohibit the formation of dye-PNA-DNA complex due to unfavorable steric hindrances, or better dye solubility in water caused by the presence of three positive charges in one dye molecule. Dyes with butyl and pentyl substituents still bind to the pre-annealed PNA-DNA duplex, although with decreasing affinity, as demonstrated by less decrease in the 556 nm absorbance as the bulk of the substituents increases. Furthermore, for $DiSC_5(3)$, the 470 nm absorbance was also decreased, compared to the 470 nm absorbance of $DiSC_2(3)$, $DiSC_3(3)$, and $DiSC_4(3)$. The approximate 86 nm blue-shift in absorbance maxima of the new band indicates that the propyl, butyl, and pentyl dyes also form higher aggregates in the presence of PNA-DNA complexes.

2. Circular Dichroism (CD)

Figure 1B:
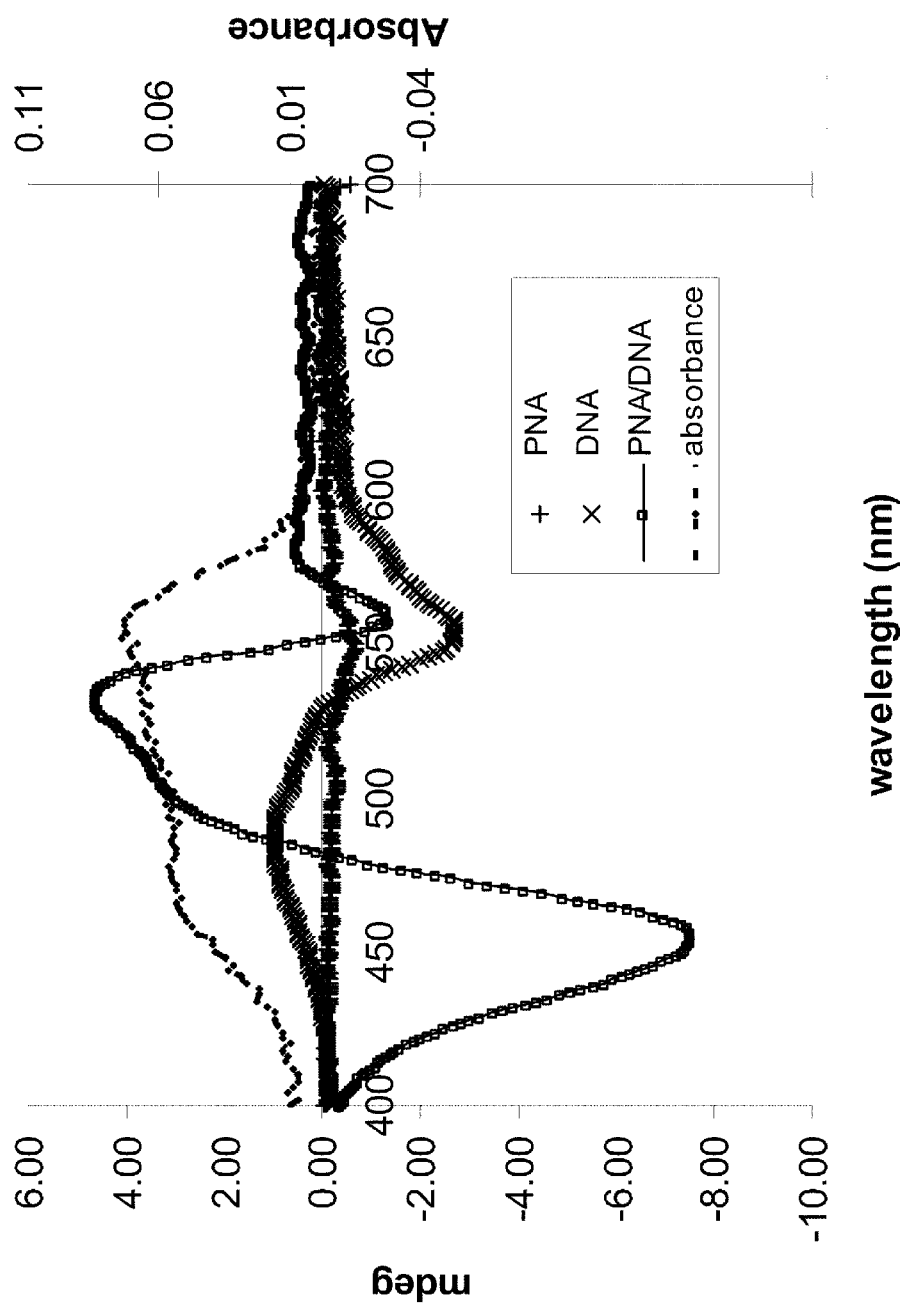
FIG. 1B is a graph of a CD spectra of $DiSC_2(3)$ in the presence of PNA, DNA or PNA-DNA duplex, (left ordinate scale). The PNA used in the study is TB23, with its complementary DNA oligo. The mixture had final concentrations of 9 μM dye, 1 μM PNA, 1 μM DNA, or 1 μM PNA-DNA duplex. UV-vis spectra of dye with the same PNA-DNA duplex is included for comparison (right ordinate scale).

$DiSC_2(3)$ is a symmetrical achiral molecule; thus, the dye alone has no CD spectra. Upon interaction of the dye with either the right-handed PNA-DNA duplex or DNA duplex, the dye adopts the chirality of the target duplex[32,38]. If the dye interacts with the helical PNA-DNA duplex, an induced CD spectrum for the resulting dye-duplex complex is produced (FIG. 1B). As expected, $DiSC_2(3)$ in the presence of PNA has no observable CD signal. $DiSC_2(3)$ combined with single-stranded DNA shows a small induced CD signal centered at about 525 nm due to the interaction of the dye with the naturally coiled DNA strand. The dimer band of $DiSC_2(3)$ has an absorbance maxima at 520 nm (FIG. 1A). Thus, these 520 nm and 525 nm bands indicate that there is a weak interaction of $DiSC_2(3)$ dimer with single-stranded DNA. Dye with PNA-DNA duplex has a much stronger multi-phase CD signal centered at about 470 nm which corresponds to the proposed aggregate band observed in the UV-vis spectra. Upon electronic excitation of a pure dimer, only the transition to one of the two splitting energy levels is permitted, dependent upon the alignment of the two molecules and only one positive signal would be predicted[39]. However, in a higher order dye aggregate, the close alignment of induced dipole moments (such as excited state dye dimers or trimers) results in additional second order energy splitting of the excited state. Thus, transitions to both the second order upper and lower energy levels are possible, and a multi-phase CD signal is produced. Therefore, the multi-phase CD signal observed with $DiSC_2(3)$ and PNA-DNA duplex indicates that $DiSC_2(3)$ interacts with the PNA-DNA duplex as a higher aggregate.

3. Fluorescence

There are 3 different interaction mechanisms of small molecules with duplexes: intercalation (and half-intercalation), groove binding and non-specific electrostatic interactions[19-23]. For DNA-DNA duplexes, all of the above interaction modes have been reported, while for PNA-DNA or PNA-PNA duplexes, only groove binding and non-specific electrostatic interactions have been reported. When a fluorescent molecule is intercalated into the base pairs of duplexes, internal rotation of the dye molecule is restricted and generally fluorescence enhancement is observed. If a single fluorescent molecule binds to the groove of the duplex, a similar fluorescent enhancement occurs. However, when the binding of an initial dye molecule facilitates the cooperative binding of a second or even third molecule and causes them to assemble in parallel, as observed in H-aggregate, the fluorescence of the dye molecules is quenched[38].

The fluorescence pattern of $DiSC_2(3)$ and $DiSC_{py}(3)$ with PNA-DNA duplexes are very different (FIG. 6). Upon binding to a PNA-DNA oligomer duplex, $DiSC_{py}(3)$ exhibits enhanced fluorescence emission, indicating intercalation or a single molecule groove binding mode of interaction. $DiSC_2(3)$, on the other hand, shows quenching of fluorescence in the presence of the PNA-DNA oligomer duplex. This indicates that $DiSC_2(3)$ binds cooperatively as an aggregate. The data from the UV-vis and CD spectra further support the formation of a $DiSC_2(3)$ aggregate on a PNA-DNA oligomer duplex. Also, the $DiSC_2(3)$-PNA-DNA complex exhibits a new fluorescence peak that is further red-shifted from the major fluorescence peak. This may be due to excimers (excited state dimers) formed within the aggregates.

II. Dye-PNA-DNA Photobleaching Reaction on Gel

This experiment was performed to determine if the decrease in the 556 nm dye monomer band and the appearance of the 470 nm band observed in solution with dye-PNA-DNA could be observed on a gel. The gel allows the separation of the free dye, the dye-PNA-DNA duplex and the DNA (with or without dye). Thus, we could also determine the interaction of each complex with light. PNA has a neutral backbone, thus in a PNA-DNA duplex, the lower molecular weight to charge ratio results in gel retardation. We used a modified non-denaturing polyacrylamide gel electrophoresis assay (PAGE) to observe the different effects of DNA vs. PNA-DNA on dye photobleaching in a gel. Upon exposure of the $DiSC_2(3)$-stained gel to light, accelerated photobleaching of $DiSC_2(3)$ occurred at positions in the gel that correspond to the location of PNA-DNA duplexes (FIG. 2, with 4 PNA and complementary DNA tested, sequences shown in Table-1). Control lanes loaded with DNA alone showed none or a very weak photobleaching at a position on the gel that corresponds to the expected position of the DNA band. Lanes loaded with the PNA-DNA duplexes showed photobleaching bands at positions that correspond to the expected positions of the PNA-DNA duplexes. These results suggest that a direct association of $DiSC_2(3)$ with the PNA-DNA duplex results in accelerated photobleaching of $DiSC_2(3)$ upon exposure to light. As this accelerated photobleaching phenomenon occurs with PNA-DNA duplexes of four different sequences, it appears to be sequence independent III. Aspects of the Dye-PNA-DNA Accelerated Photobleaching Reaction in Solution with Genomic DNA The observed interaction and accelerated photobleaching of dye $DiSC_2(3)$ in the presence of PNA-DNA duplexes can be used in the detection of DNA. A novel phenomenon has been observed; when a PNA probe (TB14), genomic DNA and $DiSC_2(3)$ were combined in buffer, and exposed to light at the aggregate absorbance wavelength of 470 nm, accelerated photobleaching was observed only when the genomic DNA contained the PNA probe target. This entire process, which results in a rapid accelerated photobleaching reaction of the dye, is termed a smartDNA assay.

1. Estimation of Amount of DNA in a Sample Using the Accelerated Photobleaching Reaction smartDNA™ reactions were set up with dye, PNA probe and various amounts of genomic DNA isolated from *M. tuberculosis*. The photobleaching experiments were carried out in microplates with a final 50 µl reaction volume for each mixture. Generally 25 µl of samples containing different amounts of DNA in 1 mM EDTA were aliquoted into each well. Cyanine dyes were then mixed with the specific PNA probe in 20 mM Homopipes, pH 5.0 buffer plus 0.1% Tween 80 and to the DNA. After an incubation of 10 minutes in dark, changes in absorbance at 556 nm as a function of light exposure time were recorded. The absorbance decreases at a greater rate in samples containing genomic *M. tuberculosis* DNA than in any of the controls. Initial rates of absorbance change (expressed in milliabsorbance units/minute) are reasonably linear for the first 4 minutes, and are proportional to the amount of target DNA present (FIG. 3, inset).

Typically, mismatched probes are used as negative controls in DNA based assays. However, due to the lack of mature probe design rationale of PNA, and also in our practice we have found that some of the PNA probes we have designed do not work as expected in the smartDNA assay; thus, using a mismatched PNA as a control yields no useful information unless it has first been shown to work in a separate genomic system. So far we have only developed a smartDNA assay for *M. tuberculosis* and have found that testing the PNAs that work in this system against other microorganisms that do not contain complementary binding sites, a more useful indicator of specificity.

2. Specificity of the Method for Detection of Genomic DNA Target Sequences

To further validate the potential utility of smartDNA for routine genomic DNA detection the specificity of the system using $DiSC_2(3)$ and the specific *M. tuberculosis* PNA probe, TB14, was tested with DNA isolated from human, *E. coli, S. aureus, S. pneumoniae, H. influenzae, N. meningitidis, P. aeruginosa* and *K. pneumoniae*. Based on genomic sequence data, in silico validation was performed to verify that the genomes of these organisms do not contain sites complementary to TB14. FIG. 3 shows the photobleaching rate of $DiSC_2(3)$ with and without the PNA probe with non-specific DNA only or with the specific *M. tuberculosis* DNA. Reactions that contained the specific (*M. tuberculosis*) DNA and the PNA probe had the accelerated photobleaching reaction. Reactions that contained non-specific DNA and the PNA probe did not show the accelerated photobleaching reaction; rather the photobleaching rates were similar to the background photobleaching rate. Furthermore, mixtures of *M. tuberculosis* DNA with non-specific DNA, (human, S. pneumoniae or S. aureus), resulted in the accelerated photobleaching reaction in the presence of the specific PNA probe at levels similar to the reactions with *M. tuberculosis* DNA alone (FIG. 9). Thus, the accelerated photobleaching reaction appears to be the result of a specific reaction occurring between $DiSC_2(3)$, the PNA probe, and its complementary DNA target. This suggests that the accelerated photobleaching can select against some single base mismatches present in potentially contaminating organisms. We have not explored this systematically with model systems.

3. Influence of Dye Structure on Accelerated Photobleaching Rate

Among the 5 carbocyanine dye derivatives, DiSC$_2$(3), the dye with ethyl substitutions, shows the accelerated photobleaching reaction in the presence of PNA and genomic DNA. The other 4 dyes, DiSC$_3$(3), DiSC$_4$(3), DiSC$_5$(3), and DiSC$_{py}$(3), exhibit substantially less photobleaching using the same conditions of PNA probe, buffer, genomic DNA, and light exposure (FIG. 4). It is not surprising that DiSC$_{py}$(3), which exhibits no 470 nm band in the presence of pre-annealed PNA-DNA duplexes, would not participate in an accelerated photobleaching reaction (FIG. 4). However, DiSC$_3$(3), DiSC$_4$(3) and DiSC$_5$(3), which do interact with pre-annealed PNA-DNA duplexes (FIG. 1A), do not exhibit the accelerated photobleaching reaction with PNA-genomic DNA complexes. This suggests that the accelerated photobleaching reaction is dependent upon a unique complex structure formed between DiSC$_2$(3), the PNA, and the DNA target. The effect of changes in the substituents at the N-3,3' position on the rate of accelerated photobleaching indicates that the substituents play a central role in the formation of the dye-PNA-DNA complex. We propose that the dye-PNA-DNA is the photosensitizer in the accelerated photobleaching reaction.

It is possible that the structure of the dye-PNA-DNA pre-annealed oligomer system might be different from that of the dye-PNA-DNA genomic DNA system. In the genomic DNA system, the PNA and dye are bound to high molecular weight double stranded DNA. A significant, and as yet unexplained, sensitivity difference exists between smartDNA reactions run on oligomer DNA targets as compared to smartDNA reactions run on genomic DNA targets. The genomic DNA targets are detectable at approximately one million fold lower concentration (femtomolar vs. nanomolar) than the oligomer DNA targets. Investigations are ongoing to understand this important difference.

IV. Photochemical Reaction Product

To obtain sufficient material for chemical characterization steady-state photolysis of a large quantity, 500 mg, of DiSC$_2$(3) was performed. Dye dissolved in aerated pH 7 phosphate buffer was exposed to the visible portion of light from a medium pressure mercury lamp for 10-12 hours, until the pink color of the dye solution was completely cleared. Two major products of photolysis were separated using column chromatography; of which only one was stable. NMR spectra indicate that during the photolysis of the dye in the presence of oxygen, 3-ethyl-2(3H)-benzothiazolone (shown in FIG. 5) was the major stable product. Thus, when pure dye was photo-fragmented, the photo-fragmentation product is consistent with the involvement of singlet oxygen. The measuring of the bleaching kinetics of the dye in the presence and absence of oxygen in irradiated dye solution additionally support this supposition. After removal of oxygen from the solution, there is a clear and distinct deviation from the zero reaction order that is typically observed for the bleaching in the presence of either air or oxygen (FIG. 7). It is believed that during the initial exposure of the argon saturated solution to light, the residual oxygen is consumed and this causes the decrease in the bleaching rate. After all the oxygen in solution is consumed the bleaching reaction stops (FIG. 7). We believe that the photochemical reaction which occurs between dye and the light activated PNA-DNA-dye complex is similar to that which occurs with pure dye alone. In reactions with dye-PNA-DNA the rate of photobleaching is significantly decreased in the presence of azide (FIG. 8), a known singlet oxygen scavenger. The background photobleaching reaction on the other hand (PNA and dye only) remains similar with or without azide present. This suggests that the background photobleaching reactions occur via a different mechanism. Characterization of the exact nature of this process is the subject of ongoing work.

All publications, patents, and patent applications cited herein are hereby incorporated by reference in their entireties, respectively, for all purposes and to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the disclosure.

REFERENCES

1. Nielsen P. E., Egholm M., Berg R. H., Buchardt O. Science 1991, 254: 1497-1500
2. Egholm M., Buchardt O., Christensen L., Behrens C., Freier S. M., Driver D. A., Berg R. H., Kim S. K., Norden B., Nielsen P. E. Nature 1993, 365(6446):566-8.
3. Kuhn H., Demidov V. V., Coull J. M., Fiandaca M. J., Gildea B. D., Frank-Kamenetskii M. D. J. Am. Chem. Soc. 2002, 124:1097-103.
4. Jensen K. K., Orum H., Nielsen P. E., Norden B. Biochemistry 1997, 36:5072-7.
5. Tomac S., Sarkar M., Ratilainen T., Wittung P., Nielsen P. E., Norden B., Gralslund A., J. Am. Chem. Soc. 1996, .118:5544-5552.
6. Weiler, Jan, Gausepohll, H., Hauser, N., Jensen, Ole N. and Hoheisel, Jörg D. Nucleic Acids Res. 1997, 25: 2792-2799
7. Lukeman P. S., Mittal A. C., Seeman N. C. Chem. Comm. (Camb). 2004: 1694-5.
8. Larsen H J, Bentin T, Nielsen P E. Biochim. Biophys. Acta. 1999 1489:159-166
9. Nulf, C. J., Corey, D. Nucleic Acids Res. 2004, 32: 3792-3798
10. Demidov, V. V., Bukanov, N. O. and Frank-Kamenetskii, M. D. Duplex DNA capture. Current. Issues in Mol. Bio. (2000) 2(1), 31-35
11. Orum H., Nielsen P. E., Egholm M., Berg R. H., Buchardt O., Stanley C. Nucleic Acids Res. (1993) 21(23): 5332-5336
12. Lohse, J., Dahl, O., and Nielsen, P. E. Proc. Natl. Acad. Sci. (1999) 96:11804-11808
13. Kaihatsu K., Braasch D. A., Cansizoglu A., Corey D. R. Biochemistry. (2002), 41 (37):11118-11125
14. Demidov, V. V., Protozanova, E., Izvolsky, K. I., Price, C., Nielsen P. E., and Frank-Kamenetskii M. D. Proc. Natl. Acad. Sci. (2002) 99:5953-5958
15. Smolina I. V., Demidov V. V., Soldatenkov V. A., Chasovskikh S. G., Frank-Kamenetskii M. D. Nucleic Acids Res. (2005) 33: e146
16. Kielkopf, C. L., White, S., Szewczyk, J. W., Turner, J. M., Baird, E. E., Dervan, P. B., Rees, D. C., Science (1998) 282:111-115
17. Wemmer D. E. Ann. Rev. Biophys. Biomol. Strut, (2000) 29:439-461
18. Glazer A. N., Rye H. S. Nature. (1992) 359(6398):859-61
19. Rye H. S., Glazer A. N. Nucleic Acids Res. (1995) 23:1215-22

20. Biver T., De Biasi A., Secco F., Venturini M., Yarmoluk S. Biophy. J. (2005) 89:374-83
21. Hannah K. C., Gil R. R., Armitage B. A. Biochemistry. (2005) 44:15924-9
22. Mikheikin A. L., Zhuze A. L., Zasedatelev A. S. J. Biomol. Struct. Dyn. (2000) 18(1):59-72
23. Yarmoluk S. M., Lukashov S. S., Ogul'Chansky T. Y., Losytskyy M. Y., Komyushyna O. S. Biopolymers. (2001) 62(4):219-27
24. Zipper H., Brunner H., Bemhagen J., Vitzthum F. Nucleic Acids Res. (2004) 32(12):e103
25. Waggoner A., Curr. Opin. Chem. Biol. (2006), 10:62-66
26. Antony T., Subramaniam V. J. Biomol. Struct. Dyn. (2001) 19(3):497-504.
27. Yin J. L., Shackel N. A., Zekry A., McGuinness P. H., Richards C., Putten K. V., McCaughan G. W., Eris J. M., Bishop G. A. Immunol. Cell Biol (2001) 79:213-21
28. Lee L. G., Chen C., Liu L. A. Cytometry (1986) 7:508-517
29. Renikuntla B. R., Rose H. C., Eldo J., Waggoner A. S., Armitage B. A. Org. Lett. (2004) 6:909-12
30. Matsui M., Kawamura S., Shibata K., Muramatsu H. Bull. of the Chem. Soc. of Japan. (1992) 65(1):71-74
31. Wittung P., Kim S. K., Buchardt O., Nielsen P. E., Norden B. Nucleic Acids Res. (1994) 22:5371-5377.
32. Smith J. O., Olson D. A. Armitage B. A. J. Am. Chem. Soc. (1999) 121, 2686-2695
33. Wilhelmsson L. M., Norden B., Mukherjee K., Dulay M. T., Zare R. N. Nucleic Acids Res. (2002) 15:30(2)e3
34. Wang M., Armitage B. A. Methods Mol. Biol. (2002) 208:131-42.
35. Wang M., Dilek I., and Armitage B. A., Langmuir. (2003), 19, 6449-6455
36. West W., Pearce S. J. Phys. Chem.(1965) 69, 1894-1903.
37. Chibisov A. K., Zakharova G. V, Görner H. Phys. Chem.y Chem. Phys. (1999). 1, 1455-1460.
38. Seifert J. L., Connor R. E., Kushon S. A., Wang M., Armitage B. A. J. Am. Chem. Soc. (1999) 121(13), 2987-2995
39. McRae, E. G., Kasha M. J. of Chem. Phys. (1958), 28: 721
40. Armitage B. Top. Curr. Chem. (2005) 253:55-76
41. Dilek I., Madrid M., Singh R., Urrea C. P., Armitage B. A. J. Am. Chem. Soc. (2005) 127: 3339-3345.
42. Santos P. F., Reis L. V., Almeida P., Serrano J. P., Oliveira A. S., Vieira Ferreira L. F., J. Photochem. Photobiol. A: Chem. (2004) 163 267-269
43. Hoebeke M., Seret A., Piette J., van de Vorst A. J. Photochem. Photobio. B. (1988) 1(4):437-46
44. Demidov, V. V., Yavnilovich M. V., Belotserkovskii B. P., Frank-Kamenetskii M. D., and Nielsen P. E., Proc. Natl. Acad. Sci. USA, (1995), 92:2637-2641
45. Bentin, T. and Nielsen, P. E., J. Am. Chem. Soc., (2003), 125(21), 6378-6379
46. Møllegaard, N. E., Bailly C., Waring M. J., and Nielsen P. E. Biochemistry, (2000), 39 (31), 9502-9507
47. Barta, C., Tamas, K., Vass, I., Hideg, K., and Hideg, E. Proceedings of the 7$^{th}$ Hungarian Congress on Plant Physiology, (2002) 46 (3-4), 149-150
48. Lion, Y., DelMelle, M., and Van De Frost, A. Nature, (1976), 263, 442-443
49. Khan, A. U and Kasha, M. Proceedings of the National Academy of Sciences, USA, (1979), 76 (12), 6047-6049
50. Mulliken, R. S., Nature (1928), 122, 505
51. Jimenez-Banzo, A, X Ragas, P Kapusta, S Nonell 2008 Photochem Photobiol Sci 7:1003-1010
52. Soh N 2006 Anal Bioanal Chem 386:532-543
53. Gomes A, E Fernandes, JLFC Lima 2005 J Biochem Biophys Methods 65:45-80
54. Zhang G, X Li, H Ma, D Zhang, J Li, D Zhu 2004 Chem Comm 2072-2073
55. Floyd, R. A., Watson, J J., Wong, P. K., Altmiller, D. H. and Rickard, R C. (1986) Hydroxyl free radical adduct of deoxyguanosine: sensitive detection and mechanism of formation. *Free Rad. Res. Commun.*, 1, 163-172.
56. Wagner, J. R., Hu, C.-C. and Ames, B. N. (1992) Endogenous oxidative damage of deoxycytidine in DNA. *Proc. Natl cad Sci. USA,* 89, 3380-3384.
57. Berger, M., Anselmino, C, Moure, U-F. and Cadet, J. (1990) High performance liquid chromatography-electrochemical assay for monitoring the formation of 8-oxo-7,8-dihydroadenine and its related 2'-deoxynucleoside. *J. Liquid Chromatogr.,* 13, 929-932.
58. Dizdaroglujvl. (1991) Chemical determination of free radical-induced damage to DNA. *Free Rad Biol. Med.,* 10, 225-242.

The invention claimed is:

1. A method for assaying an analyte comprising a nucleic acid analog binding substrate in a sample, comprising
reacting a catalytic complex comprising a nucleic acid analog, the analyte comprising the nucleic acid analog specific binding substrate, and a light reactive dye with a light stimulus,
wherein the light stimulus catalyzes a reaction that causes a decrease in the amount of the light reactive dye, and
wherein the nucleic acid analog is not labeled with any of the components of the catalytic complex; and
detecting the presence or absence or amount of singlet oxygen produced during a reaction of the catalytic complex and light stimulus.

2. The method of claim 1, comprising detecting the presence or absence or amount of a property of the singlet oxygen.

3. The method of claim 2, wherein the property of the singlet oxygen is selected from the group consisting of: infrared emission, fluorescence, electron spin resonance, calorimetry, photo ionization, mass spectroscopy, and amount of decay of the singlet oxygen.

4. The method of claim 1, wherein the nucleic acid analog is peptide nucleic acid.

5. The method of claim 1, wherein the nucleic acid analog binding substrate is DNA or RNA.

6. The method of claim 1, wherein the dye is cyanine dye.

7. The method of claim 1, wherein the dye is thiacyanine dye.

8. The method of claim 1, wherein the dye is carbocyanine dye.

9. The method of claim 1, wherein the dye is 3,3'-diethylthiacarbocyanine ($DiSC_2(3)$).

10. The method of claim 1, wherein the nucleic acid analog specific binding substrate is a nucleic acid analyte.

11. The method of claim 1, wherein the nucleic acid analog specific binding substrate is a nucleic acid molecule bound directly or indirectly to the analyte.

12. The method of claim 1, wherein the nucleic acid analog specific binding substrate is a nucleic acid molecule bound directly or indirectly to an analyte specific binding molecule.

13. The method of claim 12, wherein the analyte specific binding molecule is an antibody that specifically binds to the analyte.

14. The method of claim 12, wherein the analyte specific binding molecule is an antigen that binds to an antibody analyte.

15. The method of claim 1, wherein the nucleic acid analog is bound directly or indirectly to an analyte specific binding molecule.

16. The method of claim 1, wherein the step of detecting singlet oxygen comprises measuring a change in a singlet oxygen sensor.

17. The method of claim 1, wherein the reaction occurs at room temperature.

18. A method for assaying a nucleic acid analyte in a sample, comprising:
a. mixing the sample with a dye and an analyte-specific reporter complex comprising a nucleic acid analog complementary to the nucleic acid analyte, wherein the nucleic acid analog is not labeled with any of the components of the catalytic complex,
wherein the analyte, if present in the sample, forms a catalytic complex with the dye and the nucleic acid analog;
b. removing from the mixture analyte-specific reporter complex not bound to the analyte;
c. exposing the mixture to light stimulus, wherein the light stimulus catalyzes a reaction that causes a decrease in the amount of the dye in the mixture; and
d. detecting the presence or absence or amount of singlet oxygen produced during the reaction of the catalytic complex and light stimulus.

19. The method of claim 18, comprising detecting the presence or absence or amount of a property of the singlet oxygen.

20. The method of claim 19, wherein the property of the singlet oxygen is selected from the group consisting of: infrared emission, fluorescence, electron spin resonance, calorimetry, photo ionization, mass spectroscopy, and amount of decay of the singlet oxygen.

21. The method of claim 18, wherein the nucleic acid analog is peptide nucleic acid.

22. The method of claim 18, wherein the dye is cyanine dye.

23. The method of claim 18, wherein the dye is thiacyanine dye.

24. The method of claim 18, wherein the dye is carbocyanine dye.

25. The method of claim 18, wherein the dye is 3,3'-diethylthiacarbocyanine ($DiSC_2(3)$).

26. The method of claim 18, wherein the reaction occurs at room temperature.

27. The method of claim 18, further comprising providing additional dye following step b.

28. A method for assaying an analyte in a sample, comprising:
   a. mixing the sample with a reporter molecule or components thereof comprising a nucleic acid analog and a nucleic acid analog binding substrate that is complementary to the nucleic acid analog,
   b. simultaneously or sequentially with step (a) mixing a dye with the reporter molecule and the sample, wherein the components of the reporter molecule and the dye form a catalytic complex;
   wherein the nucleic acid analog is not labeled with any of the components of the catalytic complex,
   wherein one of the nucleic acid analog or the nucleic acid analog binding substrate components of the reporter molecule is bound to an analyte specific binding compound; and
   wherein the analyte, if present in the sample, binds to the analyte specific binding compound;
   c. removing from the mixture any reporter molecule not bound to the analyte;
   d. exposing the mixture to light stimulus, wherein the light stimulus catalyzes a reaction that causes a decrease in the amount of the dye in the mixture; and
   e. detecting the presence or absence or amount of singlet oxygen produced during the reaction of the catalytic complex and light stimulus.

* * * * *